US008920175B2

(12) United States Patent
Black et al.

(10) Patent No.: US 8,920,175 B2
(45) Date of Patent: Dec. 30, 2014

(54) METHOD AND APPARATUS FOR IDENTIFYING DIETARY CHOICES

(75) Inventors: Richard Black, Wilmette, IL (US); Todd Kevin Abraham, Glencoe, IL (US); Keith Randall Eberhardt, Succasunna, NJ (US); Linda Lee Letcher, Arlington Heights, IL (US); Nathan V. Matusheski, Gurnee, IL (US); Sandra Jean Morreale, Arlington Heights, IL (US); Kristin H. Rubin, Chicago, IL (US); Arlene Olea Sanoy, Chicago, IL (US); Barbara Ann Yehling, Geneva, IL (US)

(73) Assignee: Thrive 365 International, Inc., Westford, MA (US)

( * ) Notice: Subject to any disclaimer, the term of this patent is extended or adjusted under 35 U.S.C. 154(b) by 1009 days.

(21) Appl. No.: 12/474,155

(22) Filed: May 28, 2009

(65) Prior Publication Data

US 2009/0298021 A1 Dec. 3, 2009

Related U.S. Application Data

(60) Provisional application No. 61/056,538, filed on May 28, 2008, provisional application No. 61/142,533, filed on Jan. 5, 2009.

(51) Int. Cl.
*G09B 19/00* (2006.01)
(52) U.S. Cl.
CPC .................................. *G09B 19/0092* (2013.01)
USPC .......................................................... 434/127
(58) Field of Classification Search
CPC .................................................. G09B 19/0092
USPC ................... 434/127, 118; 707/723, 732, 784
See application file for complete search history.

(56) References Cited

U.S. PATENT DOCUMENTS

| 3,572,585 | A | 3/1971 | Weaver |
| 4,048,477 | A | 9/1977 | Hungerford |
| 4,095,274 | A | 6/1978 | Gordon |
| 4,151,668 | A | 5/1979 | Hungerford |

(Continued)

FOREIGN PATENT DOCUMENTS

| DE | 39 33 732 A1 | 4/1991 |
| DE | 100 23 141 A1 | 11/2001 |

(Continued)

OTHER PUBLICATIONS

John A. Bower; Statistics for food science III: sensory evaluation data. Part B—discrimination tests. Nutrition & Food Science, No. 2, Mar./Apr. 1996; pp. 16-22.*

(Continued)

*Primary Examiner* — Bruk Gebremichael
(74) *Attorney, Agent, or Firm* — Fitch, Even, Tabin & Flannery, LLP

(57) ABSTRACT

A method is provided for assigning a relative score number to foods. Assignment of a relative score number to foods allows consumers to select foods that will provide a desirable diet. Equations are provided which are effective to yield a predicted raw score based on measured characteristics. The predicted raw score statistically correlates to a raw score that would be determined by an actual panel. The predicted raw scores are further processed to provide a relative score number that can be easily tracked by a consumer.

4 Claims, 8 Drawing Sheets

(56) References Cited

U.S. PATENT DOCUMENTS

| | | | |
|---|---|---|---|
| 4,244,020 A | 1/1981 | Ratcliff |
| 4,310,316 A | 1/1982 | Thomann |
| 4,321,674 A | 3/1982 | Krames et al. |
| 4,689,019 A | 8/1987 | Tilney |
| 4,828,498 A | 5/1989 | Tilney |
| 4,891,576 A | 1/1990 | Jacobs et al. |
| 4,911,256 A | 3/1990 | Attikiouzel |
| 4,950,164 A | 8/1990 | Lennon-Thompson et al. |
| 4,976,622 A | 12/1990 | Clark |
| 5,178,416 A | 1/1993 | Wennik |
| 5,412,560 A | 5/1995 | Dennision |
| 5,412,564 A | 5/1995 | Ecer |
| 5,478,989 A | 12/1995 | Shepley |
| 5,558,742 A * | 9/1996 | Kiefer ................ 156/244.16 |
| 5,639,471 A | 6/1997 | Chait et al. |
| 5,640,774 A | 6/1997 | Goldman |
| 5,673,691 A * | 10/1997 | Abrams et al. ............ 600/300 |
| 5,691,927 A | 11/1997 | Gump |
| 5,704,350 A | 1/1998 | Williams, III |
| 5,726,899 A * | 3/1998 | Ferguson et al. .......... 700/231 |
| 5,819,735 A | 10/1998 | Mansfield et al. |
| 5,836,312 A | 11/1998 | Moore |
| 5,841,115 A | 11/1998 | Shepley |
| 5,890,128 A | 3/1999 | Diaz et al. |
| 6,024,281 A | 2/2000 | Shepley |
| 6,040,531 A | 3/2000 | Miller-Kovach et al. |
| 6,083,006 A | 7/2000 | Coffman |
| 6,102,706 A | 8/2000 | Khoo et al. |
| 6,246,998 B1 | 6/2001 | Matsumori |
| 6,283,914 B1 | 9/2001 | Mansfield et al. |
| 6,336,136 B1 | 1/2002 | Harris |
| 6,436,036 B1 | 8/2002 | Miller-Kovach et al. |
| 6,556,963 B1 | 4/2003 | Tetzlaff |
| 6,572,904 B2 | 6/2003 | Rhee |
| 6,585,516 B1 | 7/2003 | Alabaster |
| 6,588,670 B2 | 7/2003 | Bukowski |
| 6,623,040 B1 * | 9/2003 | Foley et al. .................. 283/67 |
| 6,635,015 B2 | 10/2003 | Sagel |
| 6,663,564 B2 | 12/2003 | Miller-Kovach et al. |
| 6,745,214 B2 | 6/2004 | Inoue et al. |
| 6,796,507 B2 | 9/2004 | Bean et al. |
| 6,817,863 B2 | 11/2004 | Bisogno |
| 6,866,873 B2 | 3/2005 | Stern |
| 6,872,077 B2 | 3/2005 | Yeager |
| 6,878,885 B2 | 4/2005 | Miller-Kovach et al. |
| 6,953,342 B2 | 10/2005 | Bisogno |
| 7,076,438 B1 | 7/2006 | Tobelmann et al. |
| 7,090,638 B2 | 8/2006 | Vidgen |
| 7,182,248 B2 | 2/2007 | Ookushi |
| 7,297,109 B2 | 11/2007 | Brown |
| 7,348,500 B2 | 3/2008 | Zhou |
| 7,361,143 B2 | 4/2008 | Kirchhoff et al. |
| 7,413,438 B2 | 8/2008 | Bisogno |
| 7,620,531 B1 | 11/2009 | Johnson |
| 7,769,635 B2 | 8/2010 | Simons-Nikolova et al. |
| 7,788,113 B2 | 8/2010 | Fuhrman et al. |
| 7,959,567 B2 | 6/2011 | Stivoric et al. |
| 7,974,881 B2 | 7/2011 | Culver et al. |
| 7,999,674 B2 | 8/2011 | Kamen |
| 8,294,581 B2 | 10/2012 | Kamen |
| 8,382,482 B2 | 2/2013 | Miller-Kovach et al. |
| 2001/0000810 A1 | 5/2001 | Alabaster |
| 2002/0015723 A1 | 2/2002 | Koenig |
| 2002/0027164 A1 | 3/2002 | Mault et al. |
| 2002/0099274 A1 | 7/2002 | Isomura et al. |
| 2002/0128992 A1 | 9/2002 | Alabaster |
| 2002/0156351 A1 | 10/2002 | Sagel |
| 2003/0059747 A1 | 3/2003 | Yoshida et al. |
| 2003/0159857 A1 | 8/2003 | Lin et al. |
| 2003/0187683 A1 | 10/2003 | Kirchhoff et al. |
| 2003/0208409 A1 | 11/2003 | Mault |
| 2003/0219513 A1 | 11/2003 | Gordon |
| 2003/0226695 A1 | 12/2003 | Mault |
| 2004/0078218 A1 | 4/2004 | Badinelli |
| 2004/0118618 A1 | 6/2004 | Davidson et al. |
| 2004/0138820 A1 | 7/2004 | Morris et al. |
| 2004/0138949 A1 | 7/2004 | Darnton et al. |
| 2004/0176666 A1 | 9/2004 | Chait |
| 2005/0055860 A1 | 3/2005 | Arrendale, III et al. |
| 2005/0113649 A1 | 5/2005 | Bergantino |
| 2005/0156032 A1 | 7/2005 | Milstein |
| 2005/0171800 A1 * | 8/2005 | Yamaguchi ................. 705/1 |
| 2005/0184148 A1 | 8/2005 | Perlman |
| 2005/0240434 A1 | 10/2005 | Wooten et al. |
| 2005/0247213 A1 | 11/2005 | Slilaty |
| 2005/0276840 A1 | 12/2005 | Mann |
| 2006/0018998 A1 * | 1/2006 | Green et al. ................ 426/87 |
| 2006/0035200 A1 | 2/2006 | Pittman |
| 2006/0074279 A1 | 4/2006 | Brover |
| 2006/0085272 A1 | 4/2006 | Case et al. |
| 2006/0165756 A1 | 7/2006 | Catani et al. |
| 2006/0189853 A1 | 8/2006 | Brown |
| 2006/0199155 A1 * | 9/2006 | Mosher .................... 434/127 |
| 2006/0229504 A1 | 10/2006 | Johnson, Jr. |
| 2006/0263750 A1 | 11/2006 | Gordon |
| 2007/0011073 A1 * | 1/2007 | Gardner et al. ............. 705/35 |
| 2007/0012324 A1 | 1/2007 | Nirkondar et al. |
| 2007/0038933 A1 | 2/2007 | Luzzatto |
| 2007/0059672 A1 | 3/2007 | Shaw |
| 2007/0173705 A1 | 7/2007 | Teller et al. |
| 2007/0179355 A1 | 8/2007 | Rosen |
| 2007/0179359 A1 | 8/2007 | Goodwin |
| 2007/0218107 A1 * | 9/2007 | Schnur et al. ............. 424/439 |
| 2007/0269557 A1 * | 11/2007 | Culver et al. ............... 426/72 |
| 2008/0033827 A1 * | 2/2008 | Kuang et al. ............... 705/15 |
| 2008/0060853 A1 | 3/2008 | Davidson et al. |
| 2008/0081840 A1 | 4/2008 | Myers et al. |
| 2008/0083825 A1 | 4/2008 | Yang et al. |
| 2009/0077007 A1 * | 3/2009 | Schwarzberg et al. ........... 707/1 |
| 2009/0191514 A1 | 7/2009 | Barnow |
| 2009/0286212 A1 | 11/2009 | Gordon |
| 2009/0298021 A1 | 12/2009 | Black et al. |
| 2010/0003647 A1 | 1/2010 | Brown et al. |
| 2010/0010318 A1 | 1/2010 | Richter |
| 2010/0047745 A1 | 2/2010 | Bergqwist et al. |
| 2010/0055653 A1 | 3/2010 | Miller-Kovach et al. |
| 2010/0136508 A1 | 6/2010 | Zekhtser |
| 2010/0216098 A1 | 8/2010 | Montgomery |
| 2010/0266995 A1 * | 10/2010 | Gordon .................... 434/127 |
| 2011/0151414 A1 | 6/2011 | Mccarthy et al. |
| 2011/0264665 A1 | 10/2011 | Mital et al. |
| 2012/0171646 A1 | 7/2012 | Chen et al. |
| 2012/0179665 A1 | 7/2012 | Baarman et al. |
| 2012/0208151 A1 | 8/2012 | Culver et al. |
| 2012/0219931 A1 | 8/2012 | Pinnisi |
| 2012/0270187 A1 | 10/2012 | Minevitz |
| 2012/0295233 A1 | 11/2012 | Cooperman |
| 2013/0004923 A1 | 1/2013 | Utter, II |
| 2013/0045467 A1 | 2/2013 | Kamen |
| 2013/0105565 A1 | 5/2013 | Kamprath |
| 2013/0108993 A1 | 5/2013 | Katz |

FOREIGN PATENT DOCUMENTS

| | | |
|---|---|---|
| EP | 1 947 583 A1 | 7/2008 |
| GB | 2 130 769 A | 6/1984 |
| JP | S57-6963 A | 1/1982 |
| JP | S60-150170 A | 8/1985 |
| JP | H06-75976 A | 3/1994 |
| JP | H09-231472 A | 9/1997 |
| JP | 2000-098898 A | 4/2000 |
| JP | 2001-160044 A | 6/2001 |
| JP | 2002-032487 A | 1/2002 |
| JP | 2002-222263 A | 8/2002 |
| JP | 2003-267443 A | 9/2003 |
| JP | 2005-092261 A | 4/2005 |
| JP | 2005-141502 A | 6/2005 |
| JP | 2006-134114 A | 5/2006 |
| JP | 2006-252209 A | 9/2006 |
| JP | 2007-133525 A | 5/2007 |
| JP | 2007-286985 A | 11/2007 |
| JP | 2009-003848 A | 1/2009 |
| WO | 86/04438 A1 | 7/1986 |

(56) References Cited

FOREIGN PATENT DOCUMENTS

| WO | 98/45766 A1 | 10/1998 |
|---|---|---|
| WO | 2008/054231 A1 | 5/2008 |
| WO | 2010/136811 A1 | 12/2010 |

OTHER PUBLICATIONS

Hungarian Intellectual Property Office Search Report and Written Opinion for Singapore Patent Application No. 201008447-3 dated Mar. 15, 2012, 15 pages.
Gal Trieu, "How many Weight Watchers Points is that?", Jul. 18, 2007, [online], [retrieved on Feb. 14, 2012]. Retrieved from the Internet: <URL: http://www.healthyweightforum.org/eng/articles/weight_watchers_points/ > (3 pages).
N. K. Christensen et al., Quantitative assessment of dietary adherence in patients with insulin-dependent diabetes mellitus, Diabetes Care, United States, May-Jun. 1983, 6(3), pp. 245-250.
C. W. Suitor et al., Planning high-carbohydrate, high-fiber diets with a microcomputer, Journal of the American Dietetic Association, United States, Mar. 1983, 82(3), pp. 279-282.
M. L. Wheeler et al., Computer-planned menus for patients with diabetes mellitus, Diabetes Care, United States, Nov.-Dec. 1980, 3(6), pp. 663-667.
J. M. Olefsky, Fructose, xylitol, and sorbitol, Diabetes Care, United States, Mar.-Apr. 1980, 3(2), pp. 390-393.
R. Spencer et al., An assessment of micronutrient status, cardiovascular risk factors and weight loss in individuals following low glycaemic index diet plans, 2006, 48 pp., Research Report No. 893.
J. Miller Jones, Nutrition, Cereal Foods World, May-Jun. 2005, 50(3), pp. 150-152.
Z. Li et al., Long-term efficacy of soy-based meal replacements vs an individualised diet plan in obese type II DM patients: relative effects on weight loss, metabolic parameters, and C-reactive protein, European Journal of Clinical Nutrition, 2005, 59(3), pp. 411-418.
K. Fatema et al., Serum glucose and insulin response to mango and papaya in type 2 diabetic subjects, Nutrition Research, Jan. 2003, 23(1), pp.9-14.
L. S. Lieberman, Part IVF. 1. The nutrients—deficiencies, surfeits, and food-related disorders: diet and chronic disease: diabetes. The Cambridge World History of Food, vol. 1, 2000, pp. 1078-1086.
J. W. Veith, The vegan-vegetarian lifestyle, Diet and Health: Scientific Perspectives, 2nd Edition, 1998, pp. 97-115.
Anonymous, IBA helps diabetics, Confectionery Production, 1995, 61(1), p. 80.
Susana R. Patton et al., Dietary adherence and associated glycemic control in families of young children with type 1 diabetes, Journal of the American Dietetic Association, Jan. 2007, 107, 1, 46(7).
Unknown Author, A dietary intervention trial for nutritional management of cardiovascular risk factors, Nutrition Reviews, Feb. 1997, v55, n2, p. 54(3).
Patrick J. Fahey et al., The athlete with type I diabetes: managing insulin, diet and exercise, American Family Physician, Apr. 1996, v53, n5, p. 1611(9).
Inga Torsdottir et al., Gastric emptying and glycemic response after ingestion of mashed bean or potato flakes in composite meals, American Journal of Clinical Nutrition, Dec. 1989, v50, n6, p. 1415(5).
S. Mercanligil et al., The role of dietary fiber in nutrition and medical nutrition therapy, Sendrom, Turkey, 2006, 18/7, pp. 49-55.
A. E. Stephen et al., Neuroendocrine Tumors of the Pancreas, Excluding Gastrinoma, Surgical Oncology Clinics of North America, United States, 2006, 15/3, pp. 497-510.
Llona A. Arteaga, The glicemic index. A current controversy, Nutricion Hospitalaria, Spain, 2006, 21/Suppl. 2, pp. 55-60.
H. S. Englert et al., Rationale and design of the Rockford CHIP, a community-based coronary risk reduction program: Results of a pilot phase, Preventive Medicine, United States, 2004, 38/4, pp. 432-441.
M. Powers, A popular diets project, Diabetes Spectrum, United States, 2005, 18/4, pp. 251-256.
M. P. Vasconcelos, Assessment of an obesity clinic in a center hospital, Acta Medica Portuguesa, Portugal, 2004, 17/5, pp. 359-366.
T. M. S. Wolever et al., Day-to-day consistency in amount and source of carbohydrate intake associated with improved blood glucose control in type 1 diabetes, Journal of the American College of Nutrition, United States, 1999, 18/3, pp. 242-247.
I. Simon-Schnass et al., Intake and supply of alpha-tocopherol in type II diabetic patients, Diabetes und Stoffwechsel, Germany, 1997, 6/Suppl. 2, pp. 16-19.
H. Hauner et al., Diagnosis and initial therapy in type 2 diabetes mellitus: Results obtained by a standardized questionnaire. 2. Initial therapy of type 2 diabetic patients, Diabetes und Stoffwechsel, Germany, 1995, 4/6, pp. 449-453.
M. Toeller, Dietetic treatment in diabetes, Therapiewoche, Germany, 1985, 35/7, pp. 732-739.
Susana R. Patton et al., Dietary adherence and associated glycemic control in families of young children with type 1 diabetes, Journal of the American Dietetic Association, United States, Jan. 2007, 107(1), pp. 46-52.
Herwig H. Ditschuneit, Do meal replacement drinks have a role in diabetes management?, Nestle Nutrition Workshop Series, Clinical & Performance Programme, Switzerland, 2006, 11, pp. 171-179, Discussion 179-181.
Jean Nagelkerk et al., Perceived barriers and effective strategies to diabetes self-management, Journal of Advanced Nursing, England, Apr. 2006, 54(2), pp. 151-158.
Paula Cristina A. Da Costa et al., Introduction of sucrose in the diet plan of persons with type 1 diabetes: its influence in the glycemic control, Arquivos Brasileiros de Endocrinologia e Metabologia, Brazil, Jun. 2005, 49(3), pp. 403-409.
Z. Li et al., Long-term efficacy of soy-based meal replacements vs an individualized diet plan in obese type II DM patients: relative effects on weight loss, metabolic parameters, and C-reactive protein, European Journal of Clinical Nutrition, England, Mar. 2005, 59(3), pp. 411-418.
Rosemary F. Hall et al., Overcoming obstacles to behavior change in diabetes self-management, Diabetes Educator, United States, Mar.-Apr. 2003, 29(2), pp. 303-311.
Wendy A. Jorgensen et al., Perceived adherence to prescribed or recommended standards of care among adults with diabetes, Diabetes Educator, United States, Nov.-Dec. 2002, 28(6), pp. 989-998.
I. Yip et al., Liquid meal replacements and glycemic control in obese type 2 diabetes patients, Obesity Research, United States, Nov. 2001, 9 Suppl 4, pp. 341S-347S.
T. M. Wolever et al., Day-to-day consistency in amount and source of carbohydrate associated with improved blood glucose control in type 1 diabetes, Journal of the American College of Nutrition, United States, Jun. 1999, 18(3), pp. 242-247.
F. X. Pi-Sunyer et al., Multicenter randomized trial of a comprehensive prepared meal program in type 2 diabetes, Diabetes Care, United States, Feb. 1999, 22(2), pp. 191-197.
C. L. Rudkin, Vegetarian diet planning for adolescents with diabetes, Pediatric Nursing, United States, May-Jun. 1999, 25(3), pp. 262-266.
T. Travis, Patient perceptions of factors that affect adherence to dietary regimens for diabetes mellitus, Diabetes Educator, United States, Mar.-Apr. 1997, 23(2), pp. 152-156.
D. A. McCARRON et al., Nutritional management of cardiovascular risk factors. A randomized clinical trial, Archives of Internal Medicine, United States, Jan. 27, 1997, 157(2), pp. 169-177.
K. Indar-Brown et al., Glycemic and insulinemic responses after ingestion of ethnic foods by NIDDM and healthy subjects, American Journal of Clinical Nutrition, United States, Jan. 1992, 55(1), pp. 89-95.
G. IRSY et al., New possibilities in the diabetic diet, Therapia Hungarica, English Edition, Hungary, 1991, 39(2), pp. 55-62.
J. W. Anderson et al., New perspectives in nutrition management of diabetes mellitus, American Journal of Medicine, United States, Nov. 28, 1988, 85(5A), pp. 159-165.
R. Stratton et al., Improved glycemic control after supervised 8-wk exercise program in insulin-dependent diabetic adolescents, Diabetes Care, United States, Sep.-Oct. 1987, 10(5), pp. 589-593.

(56) References Cited

OTHER PUBLICATIONS

E. A. Chantelau et al., Intensive insulin therapy justifies simplification of the diabetes diet: a prospective study in insulin-dependent diabetic patients, American Journal of Clinical Nutrition, United States, May 1987, 45(5), pp. 958-962.

P. A. Kendall et al., A comparison of nutrient-based and exchange-group methods of diet instruction for patients with noninsulin-dependent diabetes, American Journal of Clinical Nutrition, United States, Mar. 1987, 45(3), pp. 625-637.

U. M. Kabadi, Nutritional therapy in diabetes. Rationale and recommendations., Postgraduate Medicine, United States, Jun. 1986, 79(8), pp. 145-156.

J. Stevens et al., Outpatient management of diabetes mellitus with patient education to increase dietary carbohydrate and fiber, Diabetes Care, United States, Jul.-Aug. 1985, 8(4), pp. 359-366.

R. A. Lorenz et al., Diet-related knowledge, skill, and adherence among children with insulin-dependent diabetes mellitus, Pediatrics, United States, May 1985, 75(5), pp. 872-876.

\* cited by examiner

FIG. 5

```
Food or Non-Alcoholic Beverage
              ↓
┌─────────────────────────────┐
│ Measure:                    │
│ Total fatty acids (g)       │
│ Sodium (mg)                 │
│ Sugar (g)                   │
│ Carbohydrates (g)           │
│ Fiber (g)                   │
│ Calcium (% Daily Value)     │
│ Saturated Fatty Acids (g)   │
│ Trans Fatty Acids (g)       │
└─────────────────────────────┘
              ↓
┌─────────────────────────────┐
│        EQUATION             │
│ 16, 17, 18, 19, 20, 21 or 22│
└─────────────────────────────┘
              ↓
      ┌──────────────┐
      │  RAW SCORE   │
      └──────────────┘
              ↓
┌─────────────────────────────┐
│   ROUND TO THE NEAREST      │
│   NON-NEGATIVE INTEGER      │
└─────────────────────────────┘
              ↓
┌─────────────────────────────────┐
│ Category Score (Relative Score) │
└─────────────────────────────────┘
```

METHOD AND APPARATUS FOR IDENTIFYING DIETARY CHOICES

This application claims the benefit of U.S. Provisional Application No. 61/056,538, filed May 28, 2008 and U.S. Provisional Application No. 61/142,533, filed Jan. 5, 2009, both of which are incorporated in their entirety herein by reference.

The invention relates to methods and apparatus for rating choices, such as methods and apparatus for rating foods to aid in selection of foods that will provide a healthy balanced diet. More particularly, a method and apparatus are provided for assigning a relative score to foods which allows consumers to select foods that will provide a diet meeting dietary guidelines, such as for example, guidelines established by the American Diabetes Association and the Dietary Guidelines for Americans.

BACKGROUND

Expert panels are often utilized to evaluate the desirability of various choices, especially for example dietary choices. In most cases, these expert panels can only evaluate a limited number of items as compared to the vast (and ever increasing) number of candidate items available to consider. Unfortunately, it can also be very difficult to leverage what expert evaluations may be available for a few items. This is complicated further by the fact that experts do not necessarily agree in all cases with one another regarding the relative desirability of a given food item for inclusion in a given diet program. Hence, information regarding the desirability of choosing one item over another, especially items which have not been evaluated by the panel, may not be apparent from the actual information provided by the expert panel.

Consumers are often interested in making healthy food choices. Many consumers need to make food choices that will help them maintain a diet for various health related reasons. For example, there are significant health advantages in keeping blood glucose levels (equivalently, blood glucose concentrations) within certain limits.

Currently, patients suffering from diabetes as well as individuals who are trying to eat a healthy diet are often instructed to follow a complex diet exchange system or count carbohydrates or calories. These systems tend to be difficult and frustrating for individuals to follow.

SUMMARY

A method and apparatus are provided that are effective for rating various choices and/or identifying (or facilitating identification of) more desirable choices from multiple choices, especially for example, dietary choices. The method provides for a prediction of desirable and undesirable choices that would be made by a panel of informed domain representatives. In a preferred embodiment, a forced choice comparison process is conducted with a panel. The forced choice comparison process generates a preference score, referred to herein sometimes as a raw score. The panel may include (exclusively or at least inclusively) individuals in a common domain, such as for example, dietary experts. Equations are in turn developed and utilized which are effective to yield a predicted raw score based on measured characteristics. The predicted raw score statistically favorably correlates to a raw score that would be determined by an actual panel.

Raw scores are further processed to provide a relative score. In this aspect, raw scores are compressed as necessary to a range/scale that allows them to be more easily tracked. The resulting relative score provides a relatively low whole number that can be easily tallied. For example, a range of 0 to 100 may be equally divided by 7 to provide 7 categories, such that foods or beverages with a raw score between 0 and less than 14.3 are categorized as 0, foods or beverages with a raw score of between 14.3 and less than 28.6 are categorized as a 1, and so on. The number of categories utilized may be increased or decreased to provide an accurate and convenient categorization of raw scores and to make the resulting relative score both a whole number and a relatively low number (for example, a single digit number) that can be easily utilized by the consumer.

In accordance with this aspect, a method is provided for facilitating selection of desirable choices. The method includes generating relative scores for a first group of choices from a panel of informed domain representatives. At least two characteristics of each of a second group of choices are measured. The measured characteristics are used to provide predicted relative scores for the second group of choices. Measured characteristics may include carbohydrates, sugar, fiber, protein, total fat, total fatty acids, total saturated fatty acids, trans fatty acids, calcium, sodium, iron, vitamins, glycemic index, glycemic load, resistant starch, sugar alcohol, and mixtures thereof. The predicted relative scores are recorded in a tangible medium to communicate the predicated relative scores and to facilitate selection of desirable choices. Examples of informed domain representatives may include dietary experts. Recording the predicted relative scores in a tangible medium may include, for example, recording the predicted relative scores on packaging for food items, recording the score in a computer device, and recording the score in literature such as a handout or poster.

In one aspect, a method is provided for assisting a person to maintain a predetermined diet. The method includes determining a minimum and maximum relative score effective for maintaining a predetermined diet over a period of time such as for example, a single snack, a single meal, a day, a week or two weeks. Relative scores are calculated for each of a number of possible food serving choices and the relative score for each food choice for a given period of time can be tallied to provide a total relative score. Food serving choices are then identified that will provide a total relative score that is within the predetermined minimum and maximum for the desired time period.

In another aspect, relative scores for a food item may be calculated and assigned to the food item by first calculating a raw score using Equation 16A below.

$$\text{RAW SCORE} = k_0 + k_1 \times f_1(x_1) + k_2 \times f_2(x_2) + k_3 \times f_3(x_3) + \ldots \quad \text{EQUATION 16A}$$

The coefficients $k_0, k_1, k_2, k_3 \ldots$ are numerical constants which can range from $-50$ to $50$, the functions $f_1, f_2, f_3 \ldots$ are appropriate functions of the nutrient values which are themselves represented by $x_1, x_2, x_3 \ldots$. The expression $x_i$ could also represent functions of two or more nutrient values corresponding to the food item in question. The functional forms for $f_1, f_2, f_3 \ldots$ may include linear, logarithmic, exponential, trigonometric, splines, wavelets, and other monotone (and near monotone) functions, which may be increasing or decreasing. Several examples of appropriate and useful functions are described below (Equations 16-22).

A method for calculating a relative score is provided that includes the following steps:

assigning a raw score comprising a fixed value when the portion comprises a food or nonalcoholic beverage having 5 grams or less carbohydrates and less than 20 kilocalories;

for a food portion having 3 grams of carbohydrates or more, determining carbohydrate, protein, fiber, trans fatty acids, saturated fatty acids, total fatty acids, calcium and sodium, iron and vitamin and mineral values and calculating a raw score using Equation 1A or Equation 1B or Equation 1C (which equations are shown and described below);

for a food portion having less than 3 grams of carbohydrates, determining protein, saturated fatty acids, total fatty acids, and sodium values and calculating a raw score using Equation 2 (shown and discussed below);

when the portion comprises a nonalcoholic beverage having 20 kilocalories or more, determining sugar, total fatty acids, calcium, vitamin and mineral values and calculating a raw score using Equation 3 (shown and discussed below);

when the portion comprises an alcoholic beverage, determining a raw score using Equation 4 (shown and discussed below); and using the raw score to determine the relative score. Raw scores may also be calculated using Equations 5-15 as are also shown and discussed below.

In another aspect, a method is provided for labeling food items with a relative score number. The method includes calculating a relative score number using the equations set forth herein, especially Equations 16A and Equations 16-22. The food item is then labeled with its calculated relative score number.

In another aspect, an apparatus is provided that includes a container, a portion of an edible item disposed in the container, and a relative score number disposed on a surface of the container. This container can include, by one approach, packaging for the food such as a bag or a box. By another approach, this container can include a vending machine having a display such as a flat-screen display upon which the relative score number or numbers appear. Relative score numbers may be calculated using the Equations set forth herein, especially Equations 16A and Equations 16-22. The container is then labeled with its calculated relative score number.

In another aspect, an apparatus is provided that includes a memory having a series of digital computer instructions stored therein to facilitate determining a relative score for portions of various foods, non-alcoholic beverages, and alcoholic beverages. This can include, for example, using one or more of the equations described herein to calculate these relative scores. By one approach, this can include effecting batch calculations for a plurality of different items. By another approach, if desired, this can include effecting on-the-fly calculations on an as needed basis.

In another aspect, a method of predicting an actual raw score is provided. The method includes conducting forced choice paired comparisons with a panel to generate actual raw scores for a defined set of items. Equations are developed to yield predicted raw scores based on measured characteristics such that the correlation between actual and predicted raw scores is favorable in that it provides an $r^2$ of 0.5 or greater and a root mean square error value of 20 or less, and preferably, an $r^2$ of 0.6 or greater and a root mean square error value of 12 or less.

In another aspect, a method is provided for selecting foods suitable for a predetermined diet. The method includes collecting input from an expert panel regarding a set of food items. A relative score is calculated and assigned to each food item based on the collected input. Minimum and maximum total relative score numbers effective for maintaining the predetermined diet over a period of time are determined. Foods are selected that provide a total relative score within the minimum and maximum total relative score number.

Those skilled in the art will recognize and appreciate that the teachings herein are highly scalable and will readily accommodate application with respect to essentially any edible or palatable material including solid foods and beverages (including both alcohol-based beverages and alcohol-free beverages), both processed or raw. It will further be appreciated that relatively complex ranking and rating criteria (including both objective and relatively subjective criteria) are readily accommodated while preserving, in the end, a highly intuitive and useful index result that consumers are capable of appreciating and applying with little or no training.

BRIEF DESCRIPTION OF THE DRAWINGS

FIG. 5 illustrates a flow chart for an eating system for people with diabetes.

DETAILED DESCRIPTION

Figure 1:
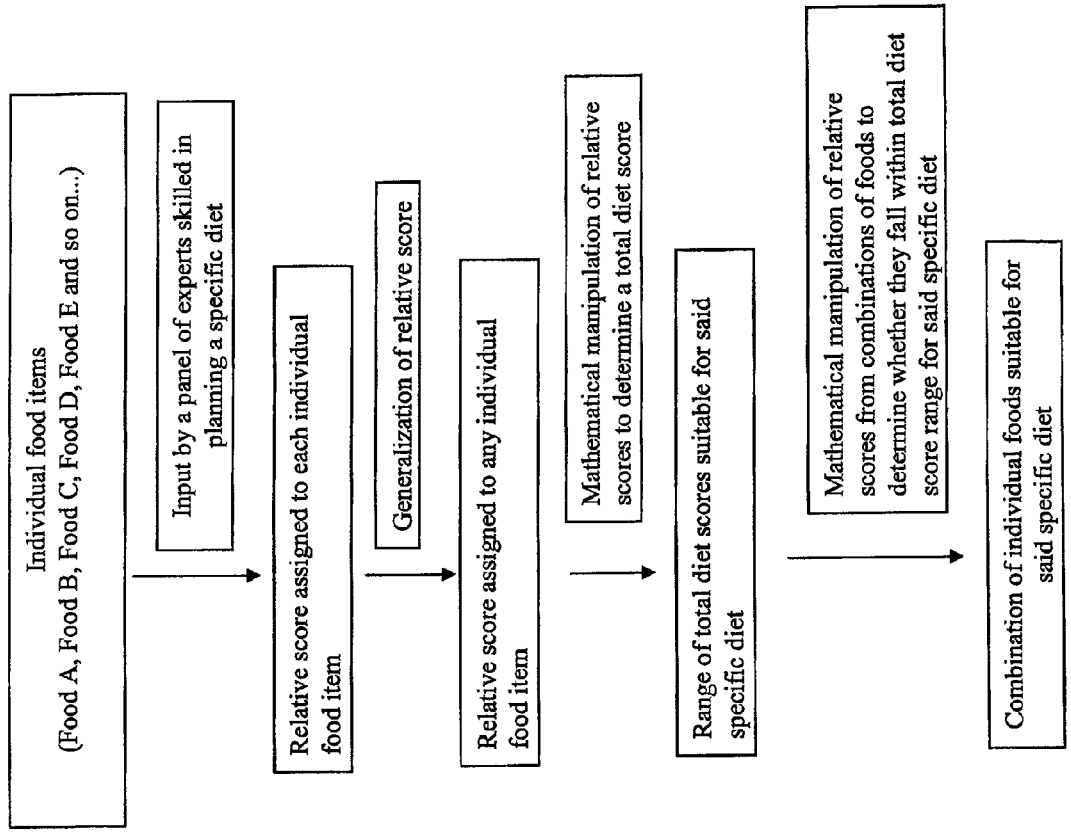
FIG. 1 generally describes a system for making dietary choices.

FIG. 1 provides a general description of a system for making dietary choices. As shown in FIG. 1, a panel of experts skilled in planning a specific diet effective for providing a desired result assign a relative score to each individual food item. These relative scores are generalized such that a relative score can be assigned to any food item, even those which have not been specifically scored by the panel of experts, by measuring at least two characteristics of the food item. Relative scores of various foods are used to determine a range of suitable scores for a specific type of diet. Examples of specific diets or predetermined diets effective for providing a desired result may include diets suitable for diabetes, heart disease, blood pressure management, metabolic syndromes, weight management, healthy aging, cognition and cancer prevention. An individual can then use this information to select combinations of foods suitable for a specific diet.

Figure 2:
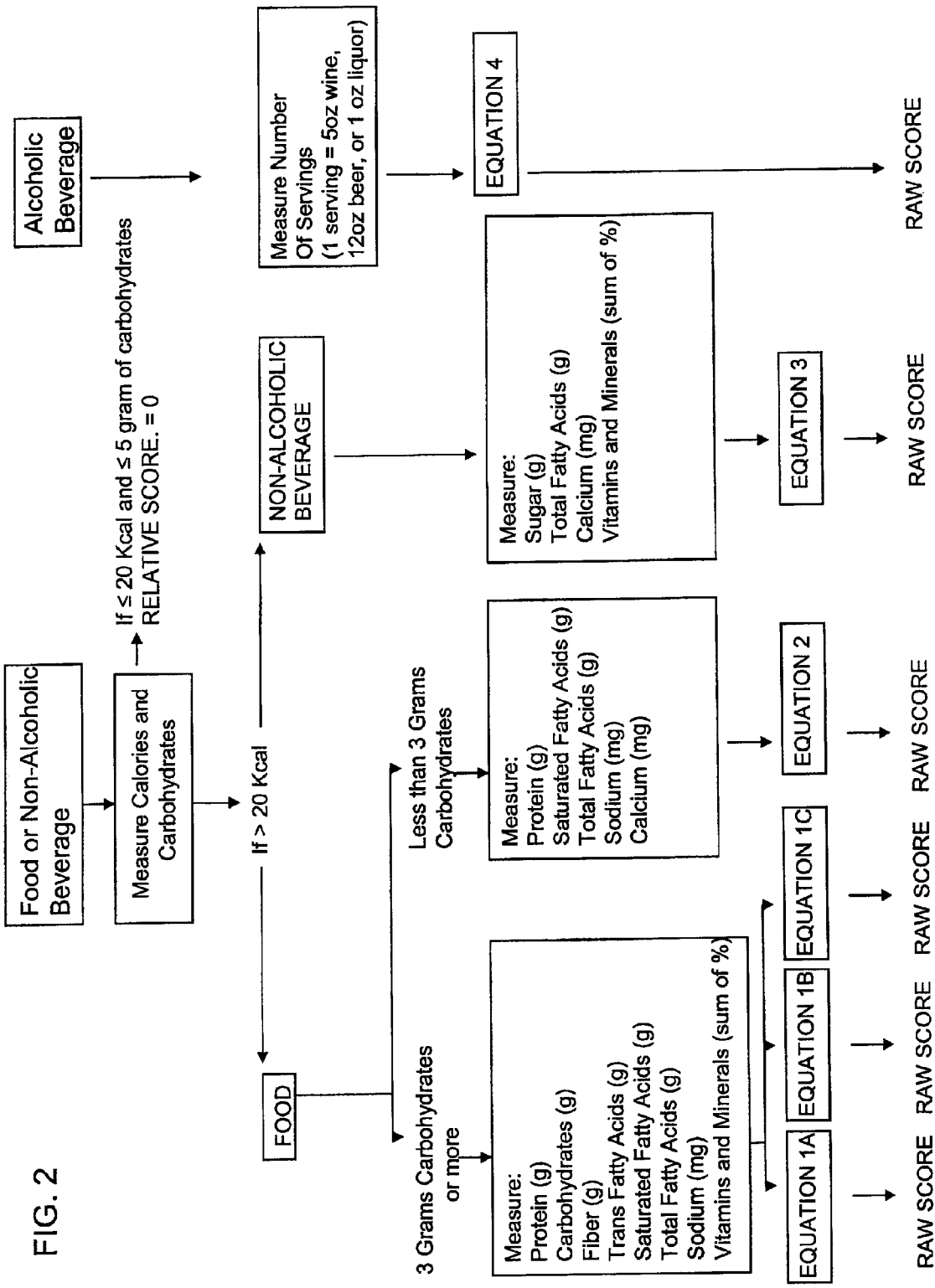
FIG. 2 illustrates a flow chart for determining a raw score of a food, non-alcoholic beverage or alcoholic beverage.

As illustrated in FIG. 2, scores used for providing a relative score number can be determined for a food or a non-alcoholic or alcoholic beverage. Foods or non-alcoholic beverages having less than about 5 grams of carbohydrates and less than 20 kilocalories are assigned a relative score of zero. Food and non-alcoholic beverages having less than 20 kilocalories are given a zero score in accordance with the "free food" designation by the American Diabetes Association Choose Your Foods system.

Total carbohydrates are measured for food having 20 kilocalories or more. Foods having three grams of carbohydrates or more are further measured to determine grams of protein, grams of fiber, grams of trans fatty acids, grams of saturated fatty acids, grams of total fatty acids, mgs of sodium and a sum of a percent daily value (% D, based on a 2000 kilocalorie diet) for vitamins A, C, and minerals iron and calcium. A raw score is calculated with Equation 1A, 1B or 1C (as shown below) using the measured amounts. Foods having less than three grams of carbohydrates are further measured to determine grams of protein, grams of saturated fatty acids, grams of total fatty acids, mg of calcium and mg of sodium. A raw score is calculated with Equation 2 (shown below) using the measured amounts.

Non-alcoholic beverages having 20 kilocalories or more are further measured for grams of sugar, grams of total fatty acid, mg of sodium and a sum of a % DV (based on a 2000 kilocalorie diet) for vitamins A, C, and minerals iron and calcium. A raw score is calculated with Equation 3 (shown below) using the measured amounts.

For alcoholic beverages, a number of servings is determined and a raw score is calculated from Equation 4 (shown below). One serving is defined as 5 ounces of wine, 12 ounces of beer, or 1 ounce of liquor.

All measurements made herein are made using techniques known in the art.

Figure 3:
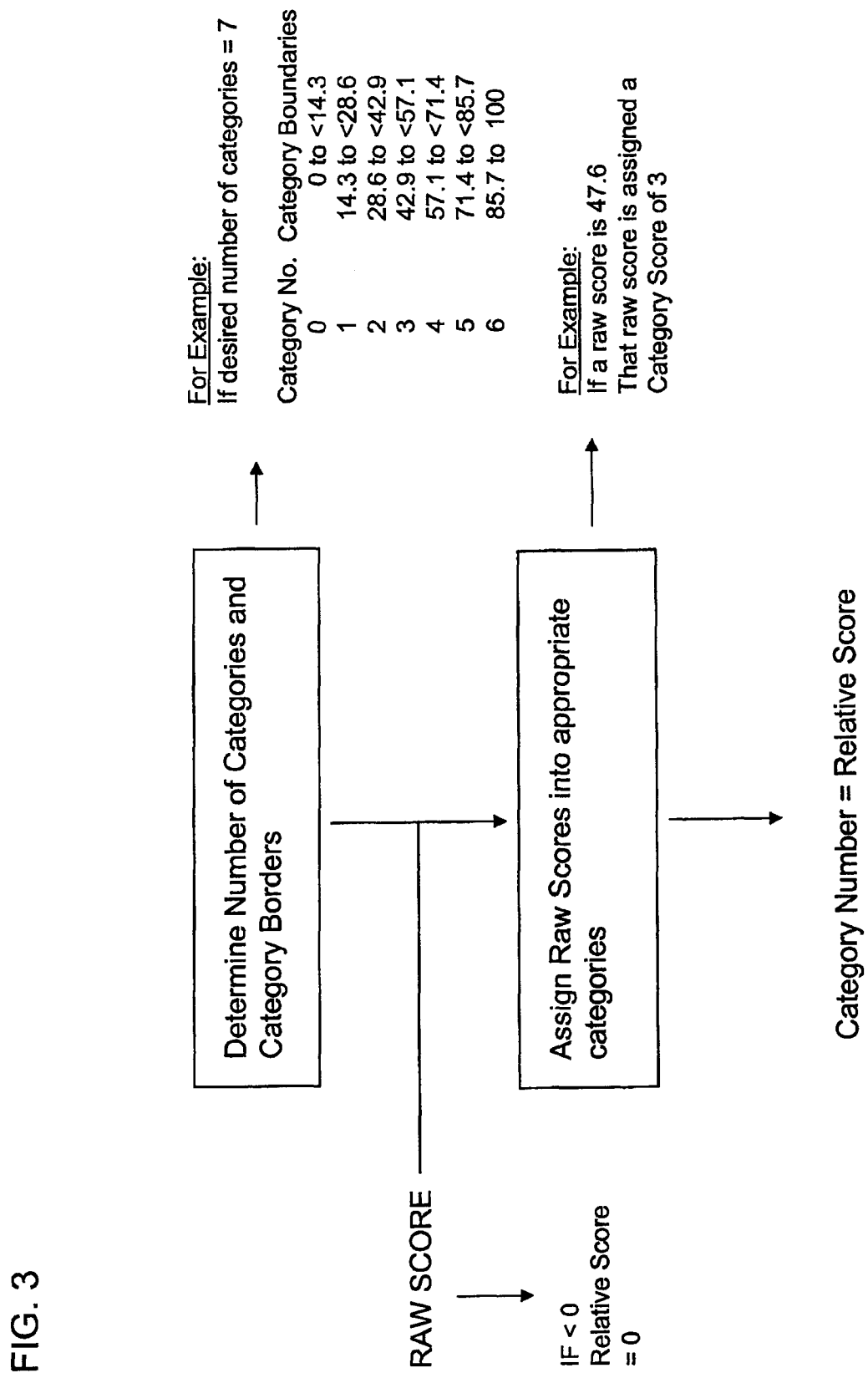
FIG. 3 illustrates how a raw score may be converted into a relative score number.

As shown in FIG. 3, raw scores are further processed to provide a relative score. For example, a number of desired categories and category boundaries are determined. As further described herein, any number of desired categories may be utilized. Further, categories may have boundaries of equal sizes or the size of the categories may be extended on the high or low ends. Raw scores are assigned into an appropriate category. The category number becomes the relative score.

Figure 4:
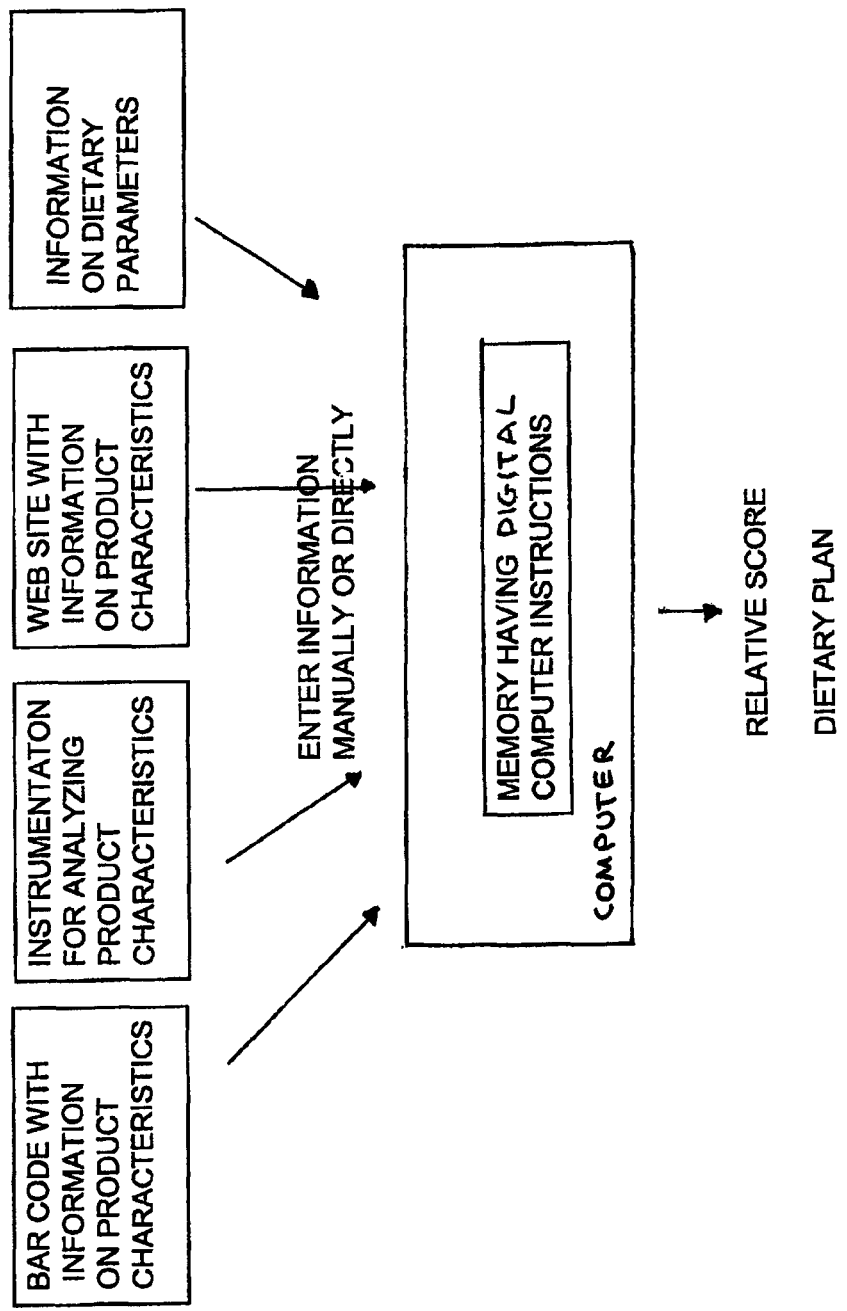
FIG. 4 comprises a block diagram that depicts how information may be acquired and utilized to provide a relative score and/or a dietary plan.

As illustrated in FIG. 4, information for determining a relative score and ultimately a dietary plan may be acquired in any number of ways. For example, products may include bar codes which provide product information or which can be utilized to gain access to such information. Product characteristics may be provided from instrumentation which analyzes products. Product information may be obtained from a web site. In addition, desired dietary parameters may be provided. Any of this or any other information may be provided directly to a computer or input into a computer using any known method. A computer having access to a memory having appropriate instructions stored therein may then calculate a relative score and/or a dietary plan using such information and upon applying the specific teachings presented herein.

Figure 8:
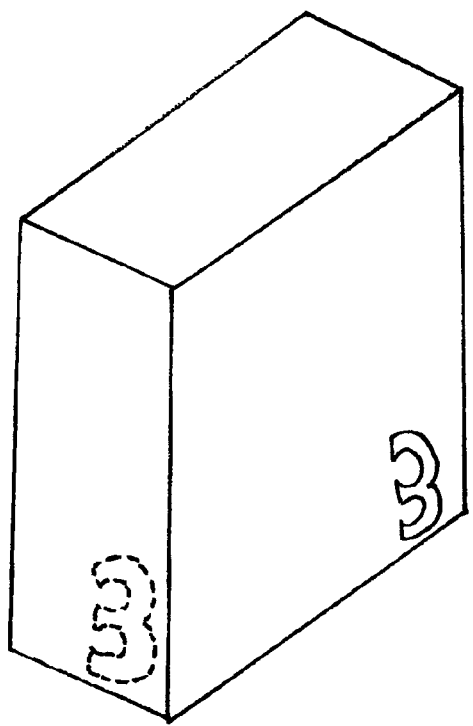
FIG. 8 illustrates a package with a relative score number.
Figure 9:
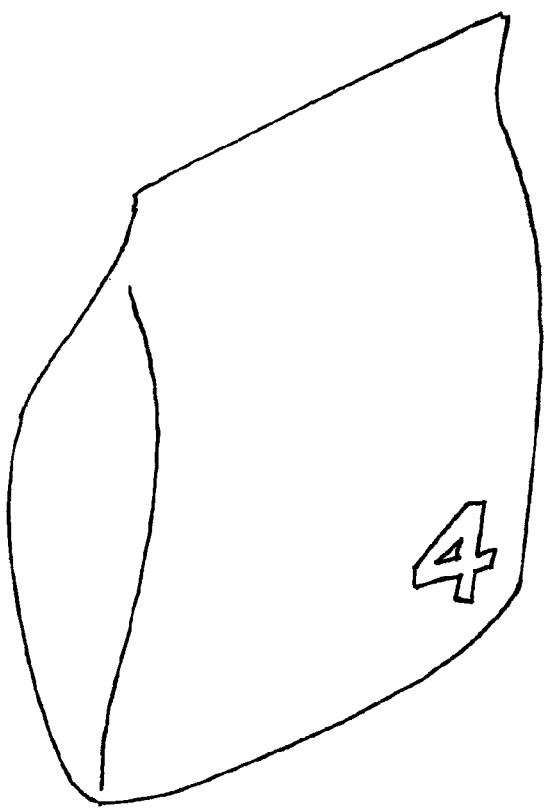
FIG. 9 illustrates a bag type of package with a relative score number.

The resultant calculated relative score number can then be displayed in some manner that is useful to the dieter. This can comprise, for example, placing the relative score number for a given food item on the container that contains that food item. By way of illustration and without intending any limitations in these regards, as shown in FIG. 8 this can comprise disposing the relative score number (in this case, a "3") on a cardboard box that contains some predetermined portion (such as one or more serving portions) of the edible item. This relative score number can be sized, placed, and/or colored to facilitate its being readily noticed by the consumer. With this in mind, if desired, the relative score number can be shown in more than one location on the box as suggested by the "3" shown in phantom lines. As another non-limited example in these regards, and referring now to FIG. 9, the relative score number can be similarly placed on an outer surface of a bag that contains the food item.

Determination of Actual Raw Scores

A panel of approximately 315 participants (the experts) deemed expert in diet counseling for people with type 2 diabetes were recruited to assess 250 different foods and beverages regarding suitability for inclusion in the diet of a person with type 2 diabetes. These experts consisted of certified diabetes educators (CDEs) and dietitians who currently counsel diabetic patients and who have practiced in this area for at least 5 years. Using the psycho-physical approach of Thurstonian forced choice paired comparisons, and an incomplete random block design, each food was presented as one food in a pair of foods and the expert was asked to choose which of the two foods presented was more suitable for inclusion in the diet of someone with type 2 diabetes. For each pair of foods presented a choice had to be made before the next pair of foods would be presented (hence, "forced choice").

In one aspect, all 250 foods were evaluated in this manner such that each food was paired with between about 42 and about 59 other items from the list of 250 foods. Each pair was then submitted to a forced choice evaluation by a least about 15 experts. An actual expert judgment per pair ranged from about 15 to about 45. Experts were not given any opportunity to indicate the reason or rationale for the choice.

All foods were presented in a similar manner. Specifically, the angle and lighting of the photos were close to identical, the dinnerware was of a single design without pattern, the amount of a food shown was the Reference Amount Customarily Consumed, or RACC, or where appropriate, a single serving as purchased for ready to eat foods as typically purchased, and the Nutrition Facts Panel (NFP) for that serving of food was presented alongside the image of the food. The information contained within the NFP was: serving size (g), calories, calories from fat, total fat (g, % DV), saturated fat (g, % DV), trans fat (g), cholesterol (mg, % DV), sodium (mg, % DV), total carbohydrate (g, % DV), dietary fiber (g, % DV), sugars (g), protein (g), vitamin A (% DV), vitamin C (% DV), calcium (% DV), iron (% DV), all based on a 2000 calorie diet. In addition, each image was accompanied by a suitably descriptive title, e.g. All Beef Hotdog on Whole Wheat Bun.

Following the technique of Thurston, the likelihood that a given food would be chosen as more appropriate than all other foods can be determined, ranging from 0 to 100.00 (i.e. never chosen as more appropriate to always chosen as more appropriate). Thus not only are the 250 foods ranked in an ordinal manner, but the distance between adjacent foods can vary. In other words, whereas a straightforward ranking would result in each food being 100/250 units away from its neighbors, Thurstonian comparisons uncover the cognitive distance between foods on the scale.

To illustrate this point, if we were to rank a serving of oatmeal, a serving of fruit, and a chocolate candy bar in terms of appropriateness for inclusion in a diabetic diet, we would likely have a ranking from best to worst of:

Oatmeal Fruit Candy Bar

However, it is immediately obvious that the perceived difference (the cognitive distance) between the sugarless oatmeal and the sugar-bearing fruit is much less than that between the sugar-bearing fruit and the sugar-laden candy bar. The Thurstonian approach allows for quantification of these cognitive distances.

By inverting the scale, a score can be assigned (called the raw score) to each of the 250 foods, such that a low score is more desirable, a high score less so. Since these scores are derived from the combined independently assessed opinion of approximately 315 experts, the raw score represent the most appropriate relative score for a food.

Determination of Predicted Raw Scores

Since an expert is likely using a variety of information about a food to make a choice, and since it is possible or even likely that two experts will differ in their choice of which information to use and the weight assigned to different pieces of information, it would be extremely difficult to obtain agreement among experts on these points. Therefore, all available information about a food, as well as information that might not be commonly known but could be known to an expert, was assumed to contribute to the decision process in the forced choice comparison. This information was captured in a data file in order that statistical analyses could be conducted to determine what information about a food could be used to most reliably and accurately predict the raw score of that food. Stepwise regression was used to develop predictive equations, with as few as 3 variables to as many as 17 variables.

Information which could potentially be used in such a regression included all information in the NFP as seen by the experts, as well as mono-unsaturated fat (g), poly-unsaturated fat (g), potassium (mg), insoluble fiber (g), soluble fiber (g), individually all B vitamins including folic acid (% DV based on a 2000 kilocalorie diet), vitamins A, D, E (% DV based on a 2000 kilocalorie diet), minerals Mg, and P, which were not seen by the experts but could have been known by the experts and so used in the decision process. Additionally, combinations of the various pieces of information were also permitted as variables in the regression analysis (e.g. saturated fat (g) plus trans fat (g), total fat (g) plus carbohydrates (g) plus protein (g), Ca (% DV) plus iron (% DV) plus vitamin A (% DV) plus vitamin C (% DV), to name a few), as were transformations of these variables (square root, natural log, exponent, and so forth).

Through repeated analysis, using an understanding of nutrition, and with a desire to develop the strongest, most reliable and accurate predictive equations or algorithms that could be used in the development of new foods, the algorithms or equations described herein were developed. In this aspect, equations should provide an Rsquare value of 0.5 or greater and RMSE (root mean square error) of 20 or less, in an important aspect, an Rsquare value of 0.6 or greater and RMSE (root mean square error) of 12 or less, to reasonably predict values that would be assigned by an actual expert panel.

The following algorithms were developed to predict the raw scores of the 250 foods:

| | |
|---|---|
| Equations 1A, 1B, 1C | Foods with at least 3 g of carbohydrates |
| Equation 2 | Foods with less than 3 g of carbohydrates |
| Equation 3 | Beverages |

Terms used in the equations are defined as follows. Any number of these characteristics may be used.

| Term | Meaning |
|---|---|
| carb | carbohydrates in grams |
| sugar | sugar in grams |
| fiber | fiber in grams |
| fatT | total fatty acids in grams |
| fatS | saturated fatty acids in grams |
| TFA | trans fatty acids in grams |
| calc | calcium in mg |
| sod | sodium in mg |
| prot | protein in grams |
| vit | sum of the % DV (based on a 2000 kilocalorie diet) for vitamins A, C, and minerals iron and calcium |

Equation 1A:

7-variable model for foods with at least 3 g of carbohydrates.

$$\text{Raw Score} = k1 + k2 \cdot \sqrt{\text{sod}} - k3 \cdot \sqrt{\text{fiber}} - k4 \cdot \sqrt{\text{prot}} + k5 \cdot \sqrt{\text{TFA} + \text{fatS}} + k6 \cdot \sqrt{\text{carb} + \text{prot} + \text{fatT}} - k7 \cdot \sqrt{\text{vit}} - k8 \cdot \text{carb}$$

| Constant | Range | Preferred |
|---|---|---|
| k1 | 0 to 15 | 4.4933 |
| k2 | 0 to 5 | 0.47854 |
| k3 | 0 to 15 | 6.7149 |
| k4 | 0 to 30 | 9.4861 |
| k5 | 0 to 30 | 8.0378 |
| k6 | 0 to 30 | 10.786 |
| k7 | 0 to 10 | 0.7647 |
| k8 | 0 to 10 | 0.17039 | where at least 3 of the constants have a value of greater than 0.

Equation 1B:

6-variable model for foods with at least 3 g of carbohydrates.

$$\text{Raw Score} = k9 + k10 \cdot \sqrt{\text{sod}} - k11 \cdot \sqrt{\text{fiber}} - k12 \cdot \sqrt{\text{prot}} + k13 \cdot \sqrt{\text{TFA} + \text{fatS}} + k14 \cdot \sqrt{\text{carb} + \text{prot} + \text{fatT}} - k15 \cdot \text{carb}$$

| Constant | Range | Preferred |
|---|---|---|
| k9 | 0 to 20 | 0.63775 |
| k10 | 0 to 15 | 0.46815 |
| k11 | 0 to 30 | 7.9301 |
| k12 | 0 to 30 | 10.247 |
| k13 | 0 to 30 | 7.5270 |
| k14 | 0 to 40 | 11.991 |
| k15 | 0 to 10 | 0.25301 | where at least 3 of the constants have a value of greater than 0.

Equation 1C:

E7-variable model for foods with at least 3 g of carbohydrates where trans fatty acid content is not known.

$$\text{RawScore} = k99 + k100 \cdot \sqrt{\text{sod}} - k101 \cdot \sqrt{\text{fiber}} - k102 \cdot \sqrt{\text{prot}} + k103 \cdot \sqrt{\text{fatS}} + k104 \cdot \sqrt{\text{carb} + \text{prot} + \text{fatT}} - k105 \cdot \text{carb}$$

| Constant | Range | Preferred |
|---|---|---|
| k99 | 0 to 45 | 3.53534 |
| k100 | 0 to 5 | 0.48132 |
| k101 | 0 to 30 | 6.81916 |
| k102 | 0 to 20 | 9.56127 |
| k103 | 0 to 30 | 7.9144 |
| k104 | 0 to 40 | 11.21475 |
| k105 | 0 to 10 | 0.200544 | where at least 3 of the constants have a value of greater than 0.

Equation 2:

5-variable model for foods with less than 3 g of carbohydrates.

$$\text{Raw Score} = k16 + k17 \cdot \sqrt{\text{fatT}} + k18 \cdot \sqrt{\text{TFA} + \text{fatS}} + k19 \cdot \sqrt{\text{sod}} - k20 \cdot \sqrt{\text{prot}} - k21 \cdot \text{calc}$$

| Constant | Range | Preferred |
|---|---|---|
| k16 | 0 to 45 | 14.586 |
| k17 | 0 to 20 | 5.1344 |
| k18 | 0 to 20 | 3.5972 |
| k19 | 0 to 5 | 0.79163 |
| k20 | 0 to 20 | 3.0349 |
| k21 | 0 to 10 | 0.043416 | where at least 3 of the constants have a value of greater than 0.

Equation 3:
4-variable model for non-alcoholic beverages.

$$\text{Raw Score} = k22 + k23*\sqrt{\text{fat}T} - k24*\sqrt{\text{calc}} + k25*\sqrt{\text{sugar}} - k26*\sqrt{\text{vit}}$$

| Constant | Range | Preferred |
|---|---|---|
| K22 | 0 to 90 | 45.125 |
| K23 | 0 to 30 | 11.360 |
| K24 | 0 to 20 | 2.7076 |
| K25 | 0 to 20 | 6.6295 |
| k26 | 0 to 20 | 1.6514 | where at least 3 of the constants have a value of greater than 0.

Equation 4:
model of alcoholic beverages.

$$\text{Raw Score} = k27 * \text{number of serving of alcoholic beverage}$$

| Constant | Range | Preferred |
|---|---|---|
| K27 | 0 to 100 | 58.7 |

In a Summary of Fit table for each algorithm there is a correlation coefficient ($r^2$) indicating strength of the predictive relationship (can range from 0 to 1.0, higher is better), an adjusted correlation coefficient ($r^2$ adjusted) which modifies the $r^2$ depending upon the number of observations in the regression, the Root Mean Square Error which is a measure of the accuracy (lower is better), the mean of all observations, and the number of observations. For foods with 3 g or more of carbohydrates, three algorithms are provided—two that have seven variables (one where trans fatty acid content is known, another where trans fatty acid content is not known) and one that has six variables. All scores are based on the RACC for that food item.

Summary of the data for Equations 1A, 1B, 1C, 2 and 3 using preferred constants are set forth below.

Equation 1A:
7-variable model for foods with at least 3 g of carbohydrates $$\text{RawScore} = 4.4933 + 0.47854*\sqrt{\text{sod}} - 6.7149*\sqrt{\text{fiber}} - 9.4861*\sqrt{\text{prot}} + 8.0378*\sqrt{\text{TFA} + \text{fat}S} + 10.786*\sqrt{\text{carb} + \text{prot} + \text{fat}T} - 0.76470*\sqrt{\text{vit}} - 0.17039*\text{carb} \quad (1A)$$

| Summary of Fit | |
|---|---|
| RSquare | 0.930578 |
| RSquare Adj | 0.928007 |
| Root Mean Square Error | 5.194836 |
| Mean of Response | 45.43088 |
| Observations (or Sum Wgts) | 197 |

Equation 1B:
6-variable model for foods with at least 3 g of carbohydrates $$\text{RawScore} = -0.63775 + 0.46815*\sqrt{\text{sod}} - 7.9301*\sqrt{\text{fiber}} - 10.247*\sqrt{\text{prot}} + 7.5270*\sqrt{\text{TFA} + \text{fat}S} + 11.991*\sqrt{\text{carb} + \text{prot} + \text{fat}T} - 0.25301*\text{carb} \quad (1B)$$

| Summary of Fit | |
|---|---|
| RSquare | 0.915021 |
| RSquare Adj | 0.912337 |
| Root Mean Square Error | 5.732374 |
| Mean of Response | 45.43088 |
| Observations (or Sum Wgts) | 197 |

Equation 1C:
7-variable model for foods with at least 3 g of carbohydrates where trans fatty acid content is not known.

$$\text{RawScore} = 3.53534 + 0.48132*\sqrt{\text{sod}} - 6.81916*\sqrt{\text{fiber}} - 9.56127*\sqrt{\text{prot}} + 7.9144*\sqrt{\text{fat}S} + 11.21475*\sqrt{\text{carb} + \text{prot} + \text{fat}T} - 0.200544*\text{carb} \quad (1C)$$

| Summary of Fit | |
|---|---|
| RSquare | 0.925065 |
| RSquare Adj | 0.92229 |
| Root Mean Square Error | 5.39718 |
| Mean of Response | 45.43088 |
| Observations (or Sum Wgts) | 197 |

Equation 2:
5-variable model for foods with less than 3 g of carbohydrates $$\text{RawScore} = 14.586 + 5.1344*\sqrt{\text{fat}T} + 3.5972*\sqrt{\text{fat}S} + 0.79163*\sqrt{\text{sod}} - 3.0349*\sqrt{\text{prot}} - 0.043416*\text{calc} \quad (2)$$

| Summary of Fit | |
|---|---|
| RSquare | 0.908986 |
| RSquare Adj | 0.894307 |
| Root Mean Square Error | 4.268039 |
| Mean of Response | 36.05331 |
| Observations (or Sum Wgts) | 37 |

Equation 3:
4-variable model for beverages $$\text{RawScore} = 45.125 + 11.360*\sqrt{\text{fat}T} - 2.7076*\sqrt{\text{calc}} + 6.6295*\sqrt{\text{sugar}} \times 1.6514*\sqrt{\text{vit}} \quad (3)$$

| Summary of Fit | |
|---|---|
| RSquare | 0.967907 |
| RSquare Adj | 0.953644 |
| Root Mean Square Error | 4.099568 |
| Mean of Response | 44.95692 |
| Observations (or Sum Wgts) | 14 |

In another aspect, equations may be used that include more or less terms as long as the Rsquare values are greater than 0.5 and the RMSE is 20 or less. Other terms that may be measured and used in the equations include Cals (calories), GI (glycemic index). Some examples of other equations that can be utilized that provide a high Rsquare and low RMSE are as follows.

Equation 5:
8-variable model:

$$\text{Raw Score} = k28 + k29*\sqrt{\text{cals}} + k30*\sqrt{\text{sod}} - k31*\sqrt{\text{fiber}} - k32*\sqrt{\text{prot}} + k33*\sqrt{\text{GI}} + k34*\sqrt{\text{TFA} + \text{fat}S} + k35*\sqrt{\text{carb} + \text{fiber} + \text{prot}} - k36*\sqrt{\text{vit}}$$

| Constant | Range | Preferred |
|---|---|---|
| K28 | 0 to 40 | 5.07998251048528 |
| k29 | 0 to 30 | 3.08655243659106 |
| k30 | 0 to 10 | 0.39720589714128 |
| k31 | 0 to 30 | 5.7926048164755 |
| k32 | 0 to 40 | 8.2403126030837 |
| k33 | 0 to 5 | 0.59193413376308 |
| k34 | 0 to 30 | 7.22441491236448 |
| k35 | 0 to 20 | 2.47726777649662 |
| k36 | 0 to 5 | 0.7054061052952 | where at least 3 of the constants have a value of greater than 0.

| Summary of Fit (based on preferred values) | |
|---|---|
| RSquare | 0.93195 |
| RSquare Adj | 0.931395 |
| Root Mean Square Error | 5.071149 |
| Mean of Response | 45.43088 |
| Observations (or Sum Wgts) | 197 |

Equation 6:
5-variable model:

$$\text{Raw Score} = k37 + k38*\sqrt{\text{sod}} - k39*\sqrt{\text{fiber}} - k40*\sqrt{\text{prot}} + k41*\sqrt{\text{TFA} + \text{fatS}} + k42*\sqrt{\text{carb} + \text{fiber} + \text{fatT}}$$

| Constant | Range | Preferred |
|---|---|---|
| K37 | 0 to 30 | 5.55540458870087 |
| K38 | 0 to 10 | 0.45731182226438 |
| k39 | 0 to 40 | 8.236932977385 |
| k40 | 0 to 40 | 8.8197607076037 |
| k41 | 0 to 40 | 8.88845433941743 |
| k42 | 0 to 40 | 9.21339238330349 | where at least 3 of the constants have a value of greater than 0.

| Summary of Fit (based on preferred values) | |
|---|---|
| RSquare | 0.911884 |
| RSquare Adj | 0.909577 |
| Root Mean Square Error | 5.821915 |
| Mean of Response | 45.43088 |
| Observations (or Sum Wgts) | 197 |

Equation 7:
4-variable model:

$$\text{Raw Score} = k43 + k44*\sqrt{\text{cals}} + k45*\sqrt{\text{sod}} - k46*\sqrt{\text{fiber}} - k47*\sqrt{\text{prot}}$$

| Constant | Range | Preferred |
|---|---|---|
| K43 | 0 to 20 | 2.58046353630472 |
| K44 | 0 to 30 | 5.20010498301525 |
| K45 | 0 to 10 | 0.48625072812575 |
| k46 | 0 to 40 | 8.3009000471813 |
| k47 | 0 to 40 | 8.6704847762015 | where at least 3 of the constants have a value of greater than 0.

| Summary of Fit (based on preferred values) | |
|---|---|
| RSquare | 0.899698 |
| RSquare Adj | 0.897608 |
| Root Mean Square Error | 6.195267 |
| Mean of Response | 45.43088 |
| Observations (or Sum Wgts) | 197 |

Equation 8:
3-variable model:

$$\text{Raw Score} = k48 + k49*\sqrt{\text{cals}} + k50*\sqrt{\text{fiber}} - k51*\sqrt{\text{prot}}$$

| Constant | Range | Preferred |
|---|---|---|
| k48 | 0 to 30 | 1.62437284640872 |
| k49 | 0 to 30 | 5.66015133153736 |
| k50 | 0 to 40 | 9.1962004078949 |
| k51 | 0 to 40 | 6.9382001155386 | where at least 3 of the constants have a value of greater than 0.

| Summary of Fit (based on preferred values) | |
|---|---|
| RSquare | 0.877904 |
| RSquare Adj | 0.876006 |
| Root Mean Square Error | 6.81755 |
| Mean of Response | 45.43088 |
| Observations (or Sum Wgts) | 197 |

Acceptable equations will have an RMSE less than about 12. This figure is based on empirical experience with menu planning in which about 12 categories were used to divide the range from 0 to 100. Some examples of other equations that can be utilized, and which provide a lower Rsquare and higher RMSE are as follows.

Equation 9:
3-variable model:

$$\text{Raw Score} = k52 + k53*\sqrt{\text{cals}} + k54*\text{carb} - k55*\sqrt{\text{fiber}}$$

| Constant | Range | Preferred |
|---|---|---|
| k52 | 0 to 40 | 8.81710431118241 |
| k53 | 0 to 30 | 3.60543550452391 |
| k54 | 0 to 10 | 0.27081834702902 |
| k55 | 0 to 50 | 11.443344392202 | where at least 3 of the constants have a value of greater than 0.

| Summary of Fit (based on preferred values) | |
|---|---|
| RSquare | 0.818428 |
| RSquare Adj | 0.815605 |
| Root Mean Square Error | 8.313843 |
| Mean of Response | 45.43088 |
| Observations (or Sum Wgts) | 197 |

Equation 10:
4-variable model:

$$\text{Raw Score} = -k56 + k57*\sqrt{\text{fatS}} + k58*\text{sod} - k59*\text{prot} + k60*\sqrt{\text{carb} - \text{fiber} + \text{prot}}$$

| Constant | Range | Preferred |
|---|---|---|
| k56 | 0 to 10 | 0.7304091450721 |
| k57 | 0 to 50 | 15.8650914166848 |
| k58 | 0 to 5 | 0.00939164579211 |
| k59 | 0 to 20 | 1.3303209449489 |
| k60 | 0 to 30 | 6.86086908729767 | where at least 3 of the constants have a value of greater than 0.

| Summary of Fit (based on preferred values) | |
|---|---|
| RSquare | 0.818571 |
| RSquare Adj | 0.814792 |
| Root Mean Square Error | 8.332165 |
| Mean of Response | 45.43088 |
| Observations (or Sum Wgts) | 197 |

Equation 11:
5-variable model:

$$\text{Raw Score} = k61 + k62 \cdot \sqrt{\text{fatS}} + k63 \cdot \text{carb} + k64 \cdot \text{prot} - k65 \cdot \sqrt{\text{prot}} - k66 \cdot \sqrt{\text{vit}}$$

| Constant | Range | Preferred |
|---|---|---|
| k61 | 0 to 75 | 30.1899062392207 |
| k62 | 0 to 75 | 17.5810089046405 |
| k63 | 0 to 10 | 0.5837157936449 |
| k64 | 0 to 10 | 0.45567486954981 |
| k65 | 0 to 30 | 5.6886855205404 |
| k66 | 0 to 20 | 1.4170049720046 | where at least 3 of the constants have a value of greater than 0.

| Summary of Fit (based on preferred values) | |
|---|---|
| RSquare | 0.819476 |
| RSquare Adj | 0.81475 |
| Root Mean Square Error | 8.333093 |
| Mean of Response | 45.43088 |
| Observations (or Sum Wgts) | 197 |

Equation 12:
6-variable model:

$$\text{Raw Score} = k67 + k68 \cdot \sqrt{\text{cals}} + k69 \cdot \text{fatS} - k70 \cdot \text{fiber} - k71 \cdot \sqrt{\text{fiber}} - k72 \cdot \text{calc} + k73 \cdot \sqrt{\text{carb-fiber+prot}}$$

| Constant | Range | Preferred |
|---|---|---|
| k67 | 0 to 30 | 5.40979065461035 |
| k68 | 0 to 20 | 3.17982018618149 |
| k69 | 0 to 20 | 1.203172246566227 |
| k70 | 0 to 20 | 1.7403988156846 |
| k71 | 0 to 30 | 4.7931109239109 |
| k72 | 0 to 5 | 0.0175448804951 |
| k73 | 0 to 20 | 1.6911060120534 | where at least 3 of the constants have a value of greater than 0.

| Summary of Fit (based on preferred values) | |
|---|---|
| RSquare | 0.820042 |
| RSquare Adj | 0.814749 |
| Root Mean Square Error | 8.333123 |
| Mean of Response | 45.43088 |
| Observations (or Sum Wgts) | 197 |

Equation 13:
7-variable model:

$$\text{Raw Score} = k74 + k75 \cdot \sqrt{\text{cals}} - k76 \cdot \text{fatS} + k77 \cdot \sqrt{\text{fatS}} - k78 \cdot \sqrt{\text{sod}} - k79 \cdot \text{calc} + k80 \cdot \sqrt{\text{carb-fiber+prot}} + k81 \cdot \sqrt{\text{carb+prot+fat}T}$$

| Constant | Range | Preferred |
|---|---|---|
| k74 | 0 to 50 | 12.5256181946947 |
| k75 | 0 to 50 | 12.4800045725714 |
| k76 | 0 to 5 | 0.0833575851909 |
| k77 | 0 to 30 | 6.78893684477268 |
| k78 | 0 to 5 | 0.0174038243731 |
| k79 | 0 to 5 | 0.0198692527924 |
| k80 | 0 to 75 | 21.2311078503332 |
| k81 | 0 to 75 | 40.908654917931 | where at least 3 of the constants have a value of greater than 0.

| Summary of Fit (based on preferred values) | |
|---|---|
| RSquare | 0.821362 |
| RSquare Adj | 0.814746 |
| Root Mean Square Error | 8.333196 |
| Mean of Response | 45.43088 |
| Observations (or Sum Wgts) | 197 |

Equation 14:
8-variable model:

$$\text{Raw Score} = -k82 + k83 \cdot \text{fatS} + k84 \cdot \sqrt{\text{fatS}} - k85 \cdot \text{sod} + k86 \cdot \sqrt{\text{sod}} - k87 \cdot \text{fiber} - k88 \cdot \text{calc} + k89 \cdot \text{GI} + k90 \cdot \sqrt{\text{carb-fiber+prot}}$$

| Constant | Range | Preferred |
|---|---|---|
| k82 | 0 to 20 | 1.0598531282242 |
| k83 | 0 to 10 | 0.35571238326255 |
| k84 | 0 to 40 | 11.9878327496585 |
| k85 | 0 to 5 | 0.0137706296504 |
| k86 | 0 to 5 | 0.50117972933279 |
| k87 | 0 to 20 | 2.0173860269672 |
| k88 | 0 to 5 | 0.0223417157976 |
| k89 | 0 to 5 | 0.11961402558121 |
| k90 | 0 to 30 | 5.61334484441492 | where at least 3 of the constants have a value of greater than 0.

| Summary of Fit (based on preferred values) | |
|---|---|
| RSquare | 0.822302 |
| RSquare Adj | 0.81474 |
| Root Mean Square Error | 8.333321 |
| Mean of Response | 45.43088 |
| Observations (or Sum Wgts) | 197 |

In another aspect, a raw score may be provided for food with at least 3 grams of carbohydrates using Equation 15 as follows.

Raw Score=$k91+k92*\sqrt{cals}-k93*\sqrt{fatT}+k94*\sqrt{TFA}+k95*\sqrt{sod}-k96*\sqrt{fiber}-k97*\sqrt{protein}+k98*\sqrt{TFA+fatS}$

| Constant | Range | Preferred |
|---|---|---|
| k91 | 0 to 20 | 2.924 |
| k92 | 0 to 30 | 4.8089 |
| k93 | 0 to 5 | 0.43276 |
| k94 | 0 to 20 | 1.8397 |
| k95 | 0 to 5 | 0.459679 |
| k96 | 0 to 30 | 7.0313 |
| k97 | 0 to 40 | 8.7050 |
| k98 | 0 to 30 | 5.3078 | where at least 3 of the constants have a value of greater than 0.

| Summary Of Fit (based on preferred values) | |
|---|---|
| RSquare | 0.92 |
| Root Mean Square Error | 5.61 |

In another aspect, the function used to calculate the raw score has the general form set forth in Equation 16A below.

RAW SCORE=$k_0+k_1 \times f_1(x_1)+k_2 \times f_2(x_2)+k_3 \times f_3(x_3)+\ldots$ Where the coefficients $k_0$, $k_1$, $k_2$, $k_3$ . . . are numerical constants which can range from −50 to 50, and in an important aspect, 0 to 50, the functions $f_1$, $f_2$, $f_3$ . . . are appropriate functions of the nutrient values, represented by $x_1$, $x_2$, $x_3$ . . . . The $x_i$ could also represent functions of two or more nutrient values corresponding to the food item in question.

The functional forms for $f_1$, $f_2$, $f_3$ . . . may include linear, logarithmic, exponential, trigonometric, splines, wavelets, and other monotone (and near monotone) functions that can be increasing or decreasing.

Several examples of appropriate and useful functions are described below. In these examples (Equations 16-22), the coefficient $k_0$=0, the other $k_i$ values are listed under the heading "Estimate," the nutrient values $(x_i)$ are listed under the heading "Term," and the functions are the identity function, $f_i(x)=x$ for all i. The $k_i$ values may range from 0 to 10 or 0 to −10, for example for fiber. These models are zero-intercept models based on n=220 foods (excluding food with kcal>300, beer and wine) and based on the original 0 to 100 scale. As described in each of the equations set forth below, to re-scale the parameters down to the scale of category scores, each parameter estimate is divided by 12.15 and then rounded to the nearest nonnegative integer.

Equation 16:

Score=[1.2574377(Carb grams)+0.3610161(Sugar grams)−2.250235(Fiber grams)+2.0426632(total Fat grams)+0.0156387(Sodium milligrams)+ 2.3307644(Sat Fat grams)]/(12.15)

6-variable model (does not use TFA):

| Summary of Fit | |
|---|---|
| Root Mean Square Error | 11.61348 |
| Mean of Response | 40.45341 |
| Observations (or Sum Wgts) | 220 |

| Parameter Estimates | | | | |
|---|---|---|---|---|
| Term | Estimate | Std Error | t Ratio | Prob > \|t\| |
| Carb | 1.2574377 | 0.098593 | 12.75 | <.0001 |
| Sugar | 0.3610161 | 0.139817 | 2.58 | 0.0105 |
| Fiber | −2.250235 | 0.473327 | −4.75 | <.0001 |
| TotFat | 2.0426632 | 0.241232 | 8.47 | <.0001 |
| Sod | 0.0156387 | 0.003812 | 4.10 | <.0001 |
| SatFat | 2.3307644 | 0.753441 | 3.09 | 0.0022 |

Equation 17:

Score=[1.2449301(Carb grams)+0.3761927(Sugar grams)−2.201028(Fiber grams)+1.9032449(total Fat grams)+0.0158553(Sodium milligrams)+ 2.654095(Sat Fat grams+trans Fat grams)]/ (12.15)

6-variable model with a single term for (SatFat+TFA):

| Summary of Fit | |
|---|---|
| Root Mean Square Error | 11.47471 |
| Mean of Response | 40.45341 |
| Observations (or Sum Wgts) | 220 |

| Parameter Estimates | | | | |
|---|---|---|---|---|
| Term | Estimate | Std Error | T Ratio | Prob > \|t\| |
| Carb | 1.2449301 | 0.096501 | 12.90 | <.0001 |
| Sugar | 0.3761927 | 0.136378 | 2.76 | 0.0063 |
| Fiber | −2.201028 | 0.468158 | −4.70 | <.0001 |
| TotFat | 1.9032449 | 0.238335 | 7.99 | <.0001 |
| Sod | 0.0158553 | 0.003718 | 4.26 | <.0001 |
| SatFat + TFA | 2.654095 | 0.685055 | 3.87 | 0.0001 |

Equation 18:

Score=[1.22775(Carb grams)+0.4028086(Sugar grams)−2.195542(Fiber grams)+1.9422293(total Fat grams)+0.0165285(Sodium milligrams)+ 2.3742248(Sat Fat grams)+4.1002263(trans Fat grams)]/(12.15)

7-variable model with TFA as a separate term:

| Summary of Fit | |
|---|---|
| Root Mean Square Error | 11.47688 |
| Mean of Response | 40.45341 |
| Observations (or Sum Wgts) | 220 |

| Parameter Estimates | | | | |
|---|---|---|---|---|
| Term | Estimate | Std Error | t Ratio | Prob > \|t\| |
| TotFat | 1.9422293 | 0.241824 | 8.03 | <.0001 |
| SatFat | 2.3742248 | 0.744785 | 3.19 | 0.0016 |
| Sod | 0.0165285 | 0.003784 | 4.37 | <.0001 |
| Sugar | 0.4028086 | 0.1392 | 2.89 | 0.0042 |
| Carb | 1.22775 | 0.098169 | 12.51 | <.0001 |
| Fiber | −2.195542 | 0.468281 | −4.69 | <.0001 |
| TFA | 4.1002263 | 1.656804 | 2.47 | 0.0141 |

Equation 19:

Score=[1.3727221(Carb grams−Fiber grams)+ 1.7677025(total Fat grams)+0.0112093(Sodium milligrams)+3.1746396(Sat Fat grams+trans Fat grams)]/(12.15)

4-variable model:

| Summary of Fit | |
|---|---|
| Root Mean Square Error | 11.79232 |
| Mean of Response | 40.45341 |
| Observations (or Sum Wgts) | 220 |

| Parameter Estimates | | | | |
|---|---|---|---|---|
| Term | Estimate | Std Error | T Ratio | Prob > \|t\| |
| TotFat | 1.7677025 | 0.242075 | 7.30 | <.0001 |
| Sod | 0.0112093 | 0.003576 | 3.13 | 0.0020 |
| SatFat + TFA | 3.1746396 | 0.689475 | 4.60 | <.0001 |
| Carb − Fiber | 1.3727221 | 0.056342 | 24.36 | <.0001 |

Equation 20:

Score=[1.1615888(Carb grams−Fiber grams)+ 0.4072277(Sugar grams)+1.8468236(total Fat grams)+0.0149536(Sodium milligrams)+ 2.8420381(Sat Fat grams+trans Fat grams)]/ (12.15)

5-variable model [uses the difference (Carb-Fiber) as a single term]:

| Summary of Fit | |
|---|---|
| Root Mean Square Error | 11.58401 |
| Mean of Response | 40.45341 |
| Observations (or Sum Wgts) | 220 |

| Parameter Estimates | | | | |
|---|---|---|---|---|
| Term | Estimate | Std Error | t Ratio | Prob > \|t\| |
| TotFat | 1.8468236 | 0.239284 | 7.72 | <.0001 |
| Sod | 0.0149536 | 0.003732 | 4.01 | <.0001 |
| Sugar | 0.4072277 | 0.136978 | 2.97 | 0.0033 |
| SatFat + TFA | 2.8420381 | 0.686473 | 4.14 | <.0001 |
| Carb − Fiber | 1.1615888 | 0.090038 | 12.90 | <.0001 |

Equation 21:

Score=[1.1728067(Carb grams−Fiber grams)+ 0.3904063(Sugar grams)+1.9836139(total Fat grams)+0.0146349(Sodium milligrams)+ 2.5446574(Sat Fat grams)]/(12.15)

5-variable model without using TFA:

| Summary of Fit | |
|---|---|
| Root Mean Square Error | 11.73127 |
| Mean of Response | 40.45341 |
| Observations (or Sum Wgts) | 220 |

| Parameter Estimates | | | | |
|---|---|---|---|---|
| Term | Estimate | Std Error | t Ratio | Prob > \|t\| |
| TotFat | 1.9836139 | 0.242318 | 8.19 | <.0001 |
| SatFat | 2.5446574 | 0.755363 | 3.37 | 0.0009 |
| Sod | 0.0146349 | 0.003826 | 3.83 | 0.0002 |
| Sugar | 0.3904063 | 0.140654 | 2.78 | 0.0060 |
| Carb − Fiber | 1.1728067 | 0.092526 | 12.68 | <.0001 |

Equation 22:

Score=[1.255412(Carb grams)+0.3807178(Sugar grams)−2.181852(Fiber grams)+1.8712286(total Fat grams)+0.0164532(Sodium milligrams)− 0.096065(Calcium % of DV)+2.8216669(Sat Fat grams+trans Fat grams)]/(12.15)

7-variable model:

| Summary of Fit | |
|---|---|
| Root Mean Square Error | 11.46567 |
| Mean of Response | 40.45341 |
| Observations (or Sum Wgts) | 220 |

| Parameter Estimates | | | | |
|---|---|---|---|---|
| Term | Estimate | Std Error | t Ratio | Prob > \|t\| |
| TotFat | 1.8712286 | 0.239751 | 7.80 | <.0001 |
| Sod | 0.0164532 | 0.003751 | 4.39 | <.0001 |
| Sugar | 0.3807178 | 0.136326 | 2.79 | 0.0057 |
| Carb | 1.255412 | 0.09685 | 12.96 | <.0001 |
| Fiber | −2.181852 | 0.468083 | −4.66 | <.0001 |
| CalcPct | −0.096065 | 0.083067 | −1.16 | 0.2488 |
| SatFat + TFA | 2.8216669 | 0.699684 | 4.03 | <.0001 |

CalcPCT is the amount of calcium in the food, as a decimal representing percentage of the daily value (% DV). For example, 25% is represented as the decimal 0.25.

Determination of a Relative Score

Raw scores represent the "appropriateness" for a food's inclusion in the diet of a person with diabetes, low scoring foods can be included more readily and hence are characterizable as being more appropriate, high scoring foods less readily and hence are characterizable as being less appropriate. In addition, these equations can be applied to all foods in the diet, beyond the 250 foods used in the initial comparisons. However, it would be extremely difficult for most individuals to keep track of the total diet score for a day if foods can be assigned scores with four significant digits and each of these scores were to be added to provide a tally for the day. Therefore, the predicted raw scores are modified to be more useful and easier to keep track of for the consumer. In one approach, this means that the relative score of a single serving (generally a RACC, or a serving as described in a recipe, a food package or other similar means) of a food can range from zero to a maximum of seven (or eight, or nine, or ten or . . . or twenty, depending on the number of categories). These scores are now called relative scores.

Any number of categories may be utilized. In this aspect, a total number of categories may range from about 5 to about 21, preferably about 6 to about 15, and most preferably about 11 or 12. The total number of categories are selected to reduce any likelihood that a food would be incorrectly categorized; allow for distinguishing between meal plans with differing nutrient needs; and provide a whole relative score number and a resulting total whole relative score number that is easy for the average adult consumer to track. As further described below, meal plans based on daily calorie intakes of 1600, 2000 and 2400 were most optimal when raw scores were assigned to 12 categories. In this aspect, consuming foods to provide a relative score of 33 will provide a total daily calorie intake of about 1600, consuming foods to provide a total relative score of 43 will provide a total daily calorie intake of about 2000, and consuming foods to provide a total relative score of 53 will provide a total daily calorie intake of about 2400.

Any raw score less than zero is assigned a raw score of zero, and any raw score greater than 100 is assigned a raw score of 100. Raw scores for each food or beverage item are compressed so that a food or beverage item may be given a relative score. Relative score numbers may range from 0 to 5, 0 to 6, 0 to 7 and so on depending on the scale being used. For example, a range of 0 to 100 may be equally divided by 7 such that foods or beverages with a raw score between 0 and less than 14.3 are categorized as 0, foods or beverages with a raw score of between 14.3 and less than 28.6 are categorized as a 1, and so on. The transition between categories can be modified to extend or contract categories on the high or low end of the scores as desired.

People with type 2 diabetes must control their intake of carbohydrates (not too much, not too little), and any system utilized must distinguish between foods that contain (digestible) carbohydrates and foods that do not. Based on guidance co-developed by the American Diabetes Association and American Dietetic Association, foods containing 5 g or less of carbohydrates per serving (e.g., 0 Carb Count in Carbohydrate Counting system) were considered to have negligible amounts of carbohydrates. In this aspect, foods having 5 grams or less carbohydrates per RACC and less than 20 kcal of energy are given a relative score of zero.

Mathematically, category borders are defined as follows:
Let N=the number of categories
p=exponent to control the shape of category borders (typically, $0.5 \leq p \leq 2$, but at least $p>0$ is required)
k=category values, which range from k=0, 1, 2, ..., N−1
Thus the category borders are defined as follows:
(4) Lower border for category "k"=$100*(k/N)^p$
(5) Upper border for category "k"=$100*((k+1)/N)^p$
A food item is placed in category k if the predicted raw Score for that food satisfies the following inequality:
(6) $100*(k/N)^p \leq$ Raw Score $< 100*((k+1)/N)^p$
When k=0, the formula for the lower border=0, though it may be useful for many application settings to actually use −10, which allows for slightly negative predicted Raw Scores. When k=N−1, the formula for the upper border=100, though it may be useful for many application settings to actually use 110, which allows for predicted Raw Scores that go slightly above 100.

Finally, an additional constraint may be applied on the categories as follows:
define an extra parameter, M, such that
M=maximum category value to be used ($1 \leq M \leq N-1$).
As a result, the category borders, as defined by (4) and (5), are modified such that when:
(6) $100*(k/N)^p \leq$ Raw Score $< 100*((k+1)/N)^p$
the food is assigned to the category=MIN(k, M), where MIN means minimum.

As a result of categorizing the predicted raw scores in this manner, the ranges of the scores are compressed so that a food can be given a relative score number ranging from 0 to 5 (or 0 to 6, or 0 to 7, or ... or 0 to 20). As p becomes increasingly less than 1.0, there is greater resolution between foods having low predicted raw scores, and less resolution for foods with higher scores. The reverse is true when p increases in magnitude above 1.0. Additionally, as N is reduced, our ability to distinguish between foods is reduced, whereas when N is increased, resolution can increase but with the potential of providing false distinctions between foods where none actually exist. Finally, as M becomes increasingly less than N−1, the higher categories are collapsed into a single category with value M. This diminishes the resolution of food differences at higher predicted raw scores.

Optimum placement of the borders for categories is important. If foods are not sufficiently distinguished, then meal plans for different individuals with differing nutrient needs would not be distinguishable. If foods are distinguished too finely, then the risk of the mis-categorizing a food based on the predicted raw score compared with the raw score, or providing false distinctions between foods increases.

Another modification is useful when the serving size of the food is different from the RACC. In these cases, the nutrients for the food are normalized to the RACC, and the food is given a predicted raw score and then a category score based on these normalized nutrients. This category score is then modified by a factor equal to the serving size divided by the RACC. Thus, if the serving size is greater than the RACC, the score will increase. If the serving size is less than the RACC, the score will decrease. All fractions of a whole number are rounded up.

Alternatively, the modification needed when the serving size of the food is different from the RACC can be obtained when the nutrients for the food are normalized to the RACC, and the food is given a predicted raw score. This raw score is then modified by a factor equal to the serving size divided by the RACC. Thus, if the serving size is greater than the RACC, the score will increase. If the serving size is less than the RACC, the score will decrease. Then a relative score based on these estimated raw scores can be obtained following the method outlined previously.

Development of Diet Plans

Methods for developing diet plans are provided which utilize both the relative score and which require choices of foods from different categories. For example, one aspect of the diet plan may require the total relative score number to equal a certain number or be within a certain range for period of time, such as one day. The total relative score number is determined by adding the relative score number for each food item consumed or to be consumed during that day. In an additional aspect of the diet plan, foods may be selected from two different categories such that certain levels of relative score number totals are achieved from selections in each food category. Food categories may be identified using any appropriate terminology. By way of a non-limiting illustrative example and in accordance with one aspect of the diet plan, foods and beverages are further designated as being a "green food" or a "blue food". Green foods are generally (but not exclusively) defined as carbohydrate-containing fruits and vegetables, grains, milk, juice, desserts and combinations of these foods. Blue foods are generally (but not exclusively) defined as meat, cheese, nuts, oils and others foods containing mostly protein or fat, as well as foods with a carbohydrate content ≤5.5 g per serving. Hence, the total relative score for a given day will include a total that represent a certain number of relative scores from green foods plus a total that represent a certain number of relative scores from blue foods. Such color coding can be used as a background color when presenting the score information, for example, on packaging for the corresponding food item. As another example, the score number itself can be presented using the corresponding appropriate color. In these regards it will be understood that numerous other possibilities are available for consideration.

It would also be possible to combine multiple colors when representing a food item (such as a multi-item entree package).

In practice, when diets were provided suitable for people with diabetes, at daily caloric intake levels of 1600 kcal, 2000 kcal, and 2400 kcal, for a period of time, such as for example for fourteen days each, and each food was scored using the appropriate algorithm to generate a predicted raw score and categorized using a simple system (N=8, p=1.0, M=N−1), the total daily score at a given energy intake varied over a range of about 15. This resulted in considerable overlap in daily scores between diets with differing energy levels. Ideally, this overlap is minimized. Therefore, utilizing the equations described above, the number of categories, N, was modified, (5 to 21), the maximum category score, M, was modified, and the exponent p modified to alter the shape of the category borders, all in order to minimize the overlap of the total daily score between the three diets. This was achieved when N=12, p=0.81, and M=11. This resulted in average scores of 33, 43 and 53 (for 1600 kcal, 2000 kcal and 2400 kcal per day respectively), with ranges typically ±5 or 6.

Operationalizing the algorithms with the categories to generate a relative score number that can be used to select foods to form a nutritionally adequate diet generated the following conditions:
1. Beverages will be reported as a Green score.
2. The average Green score represented 70-80% of the average total score in each of the 3 scored meal plans. Therefore, the consumer's assigned Green score will be approximately 75% of the total score. The daily score will be based on age, height, weight and activity level.
3. It is necessary to provide recommendations for a minimum Green score per Meal and Snack* to guarantee carbohydrate consumption in order to avoid hypoglycemia.
4. Maximum Green scores per Meal or Snack are not established nor is a recommended distribution of Blue scores over the day. This should provide greater flexibility for the consumer. It can be important, for example, not to assign all Green and Blue scores and to minimize rules and experiences that will dissatisfy the consumer.
5. Consumers should strive to consume the recommended total score per day. Any remaining score cannot be "banked" for future consumption.

| Daily Calories | 1600 | 2000 | 2400 |
|---|---|---|---|
| Avg Total Score | 33 | 43 | 53 |
| Avg Green Score | 25 | 33 | 41 |
| Minimum Green Score per Meal/Snack* | 6/6/6/3 = 21 (~78% of daily Green score) | 8/8/8/5 = 29 (~78% of daily Green score) | 10/10/10/7 = 37 (~78% of daily Green score) |
| "Flex" Green Score | 4 | 4 | 4 |
| Blue Score | 8 | 10 | 12 |

*Assumes 3 meals and 1 snack

A dietary plan could be implemented in accordance with the following guidelines.
1. Consumers would be assigned a score allocation after providing some basic physical and health information. The score will be based on height, weight, age and activity level.
2. The score allocation is divided into 2 categories:
   Green Foods (carb-containing: fruits and vegetables, grains, milk, juice, desserts and combination foods)
   Blue Foods (meat, cheese, nuts, oils and others foods containing mostly protein or fat, as well as foods with a carb content ≤5.5 g per serving).
3. Consumers will receive a recommended distribution of a proportion of the Green score allocation over the course of the day to avoid hypoglycemia.
4. Consumers will receive tips on making good choices and developing a balanced meal plan. These guidelines are consistent with the 2005 Dietary Guidelines for Americans and MyPyramid (as promulgated by the United States Department of Agriculture). Some of these guidelines include:
   Aim for 3 meals per day plus an evening snack.
   Try to distribute flexible scores throughout the day.
   Try to include at least 2 reduced fat dairy products, such as skim or 1% milk, reduced fat cheeses and reduced fat yogurt for bone health.
   Include 3 to 5 servings of fresh or frozen vegetables daily.
   Choose lower sodium canned products, such as soups, vegetables, and other products.
   Choose whole grains whenever possible.
   Choose lean meat whenever possible; aim for 2 servings of fish per week.
   Choose whole fresh fruits instead of juice to delay blood glucose response
   A food with a score of 0 is "free" only once per eating occasion (such as a given meal such as breakfast, lunch or dinner), after that, it scores 1 for each additional serving within that eating occasion.

Applications for the present methods include determinations of diets for those on the Atkins diet (or similar low-carb diets), pulmonary patients, patients with hypoglycemia, cardiovascular disease, and the like.

Diabetic Eating System

In another aspect, an eating system is provided that assigns a number to any food, based on its nutrition profile. Several iterations of Regression models (Equations 16-22) are provided with a forced zero-intercept. All of these models use strictly linear functions of nutrient data, thus the exponent can range from less than 1 to less than 5, and preferably is equal to 1.

Training data used for regression models were constrained. These regression models were developed based on a reduced data set consisting of n=220 food items, taken as a subset of the data from the original 250 food items that were evaluated by the experts (CDE's and dieticians). The remaining 30 food items that were excluded from the linear model fitting process include beer and wine, plus 28 additional food items, each of which had an energy content of more than 300 kcal. The 220 non-excluded food items all have less than 300 kcal. In effect, food items with more than 300 kcal are treated by the model as multiple servings of smaller-sized food items, and the scores are scaled proportionately. The fact that a more robust model can be developed using a subset of the original data was surprising.

As illustrated in FIG. 5, calculated raw scores provide by the models are converted to integer-valued category scores. However, the method can be refined so that when converting the predicted raw scores (decimal values on a scale from 0 to 100) into category scores (integers from 0 to about 8, or more, depending on serving size), the raw score is divided by 12.15. The resulting quotient is rounded to the nearest whole number (though it could also be consistently rounded up to the next highest integer, or consistently rounded down to the next lowest integer). The divisor 12.15 was chosen to achieve the best (most convenient) relationship between average daily scores and desirable calorie target values. Thus, for example, a daily total score of 45 corresponds to a calorie target of 2000 kcal. Choosing a different value for the divisor (ranging from 1 to 45) would result in a different daily score (much higher or much lower than 45, respectively). The further one moves from 12.15 as the divisor, the less robust and less useful is the eating system.

The present models (Equations 16-22) have the desirable property that the category score for 2 (or 3) servings of a food item will be equal to 2 (or 3) times the score for 1 serving, up to rounding error. This is true for all of the models (Equations 16-22), and is significantly different from previous versions where there was no direct proportionality between serving size and score. Although both methods lead to a scoring system that is robust and can be useful in modifying the diet, the present iterations simplify the calculations and scoring of foods with increases in serving size. Because of this linear proportional property, it is not necessary to reference standardized serving sizes of foods, such as the RACC, in order to apply the model to calculate raw scores and category scores. An additional benefit of the current model is that it will almost never produce a negative value for a predicted raw score or category score for any nutrient profile that corresponds to a real food item. Thus, all foods can be scored, the algorithm is independent of serving size, is independent of caloric content, and is the same for all foods and beverages (with the exception of alcoholic beverages).

Daily scores typical of a daily calorie level were calculated as before—scoring foods in diets that had been developed with the guidance of the Diabetes Exchange approach. Additional diet rules can be included with the eating system, to reduce the variability in macro and micro nutrient consumption, though this comes at the expense of simplicity. Each rule addition or combination of rules can influence the resulting nutrition profile of the diet, selection of specific food/beverage items and/or distribution of food. Thus there will always be trade-offs between dietary control and ease of use. There are many ways to combine these rules. The rules are described below. In the best case, the Meal and Snack rule is employed. The next rule to include which increases control with an acceptable loss of simplicity, is to assign foods to one of two categories, either with carbohydrates or without.

Rule 1: Color Coding

It has been recommended that people with diabetes try to eat about the same (reasonable) amount of carbohydrate around the same time each day. In one aspect, the eating system may add a color-coding rule to help people understand which foods are primarily carbohydrate and those that are not. Independent of the food's individual score, the nutrition information may be used to assign a color coding. For example, foods with <10 g carbohydrate and/or <50% kcal from carbohydrate could be coded with a specific color score. While foods with ≥10 g of carbohydrate could be coded with a different color score. Alternatively, color coding could be assigned based on the percentage of calories coming from carbohydrate in a given food. For example, foods where 25% (or more) of their calories are coming from carbohydrate could be assigned one color, where foods with less carbohydrate calories would have a different color. The color coding ratio of the daily score can be changed to vary the percentage of carbohydrate in the diet from 0-100% in theory, but realistically within the commonly prescribed range of 40-65% calories from carbohydrate. Color coding could also be used to denote the number of carbohydrate choices that a food represents. Other food components (total fat, saturated fat, monounsaturated fat, polyunsaturated fat, trans fat sodium, sugars, dietary fiber, protein, etc), in addition to carbohydrate could also be used to determine color coding. Incorporation of a color coding rule would therefore require the daily score being divided into two (or more) colors (e.g., green and blue). To help with distribution of the daily score throughout the day, the system can provide guidelines for the number of a particular color score used at each eating occasion. Scores would be scaled to reflect the desired daily macronutrient intake.

Rule 2: Meal and Snack Scores

People with diabetes should eat three meals each day and snacking is a common eating pattern among individuals. To balance meal and snack size throughout the day, the daily score could also be divided into an individual meal and snack score. Similarly, individual color-coded scores (as in Rule 1) could be subdivided into individual meal and snack scores. Finally, meal and snack scores can be specified for one or more color-coded scores, while one or more remaining color coded scores can be distributed freely over the course of the day for added flexibility. Scores would be scaled to reflect the desired daily macronutrient intake. For example, if a daily score was 45, this could be split across three meals and one snack as meal scores of 13 (3×13=39) and a snack score of 6.

Rule 3: Fruit and Vegetable Requirements

Adding a daily fruit and vegetable requirement could also influence the resulting nutrition profile of the diet. Fruit and vegetable requirements would be scaled according to daily calorie level and/or MyPyramid recommendations, thus each score level might have a different number of fruits and vegetables that they would be advised to consume throughout the day. For example, a score level of 45 could have a fruit requirement of 4 servings and vegetable requirement of 5 servings per day.

Rule 4: Dietary Plan Based on Green and Blue Foods as Described Previously.

The above mentioned rules could be combined in a variety of ways:
1. Each rule could be used alone
2. Two rules could be used in combination
3. Three (or more) rules could be used in combination
4. All rules could be used
5. None of the rules could be used (daily score alone)

Rules may also be added in a stepwise fashion, where individuals begin the system with a daily score (or other rule) alone and rules are added depending on the individual's personal needs.

Ranges for Meal and Snack Distribution

Daily Score level may be variably distributed among up to 8 eating occasions over the course of a daily meal plan. Eating occasions may be divided into meals and snacks, where meals are defined as having a higher Relative Score than snacks, and snacks are defined as having a lower Relative Score than meals.

Ranges for Deviation from Score

Some deviation from assigned scores may be acceptable, while still maintaining the utility of the system for planning a satisfactory diet for individuals with type-2 diabetes:

Deviation from an assigned eating occasion (meal or snack) score in the range of 0-40%.

Deviation from an assigned daily score in the range of 0-25%.

Diet Planning Data

Both sets of dietary planning data described below were collected using the "zero intercept linear model" (Equation 16).

Diet Planning Session #1

Methods: A database containing 661 commonly consumed foods was created, based on the USDA key foods list (Haytowitz et al, 2002 *J. Food Comp. Anal.*). Each food was assigned a Relative Food Score using Equation 16. A group of 13 individuals, composed of 5 men and 8 women, was randomly assigned Daily Scores corresponding to various calorie levels (Table 1). The individuals were asked to plan all meals and snacks for each day of a 2 week period, using only the Relative Food Scores and Rules 1-3 (blue/green, meal/snack, and fruit/vegetable) as the basis for diet planning. During this session, if more than 3 zero-scoring foods were used, each additional zero-scoring food was assigned a score of 1. Healthy eating guidelines (as described elsewhere) were also provided. The resulting diet plans were subsequently summarized for their energy and nutrient content on the basis of average daily intake over the 2-week dietary planning period.

TABLE 1

Daily Scores corresponding to daily energy requirements

| Daily Energy Requirement (kcal) | Number of Individuals | Daily Score | Green Score | Blue Score | Required Fruit Servings | Required Vegetable Servings |
|---|---|---|---|---|---|---|
| 1600 | n = 3 | 36 | 27 = 3 Meals @ 8 each + 1 Snack @ 3 | 9 Across the day | 3 | 4 |
| 2000 | n = 4 | 45 | 34 = 3 Meals @ 10 each + 1 Snack @ 4 | 11 Across the day | 4 | 5 |
| 2400 | n = 3 | 55 | 42 = 3 Meals @ 12 each + 1 Snack @ 6 | 13 Across the day | 5 | 6 |
| 3000 | n = 3 | 72 | 56 = 3 Meals @ 15 each + 1 Snack @ 11 | 16 Across the day | 5 | 6 |

Figure 6:
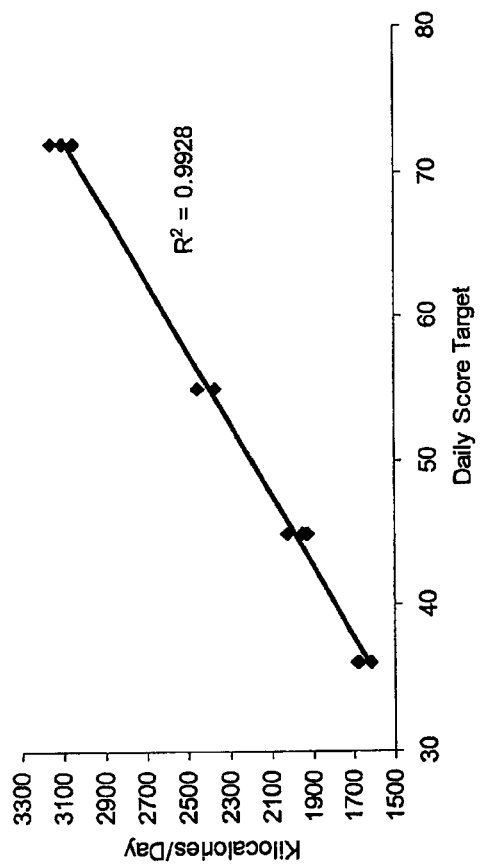
FIG. 6 shows a correlation of energy content to score target for daily meal plans, averaged across 2 weeks.

Results: Diet plans created by these individuals using the novel scoring system were satisfactory in their energy content and macronutrient profile. Energy content of the diet plans closely reflected the target energy intake levels prescribed by the assigned scores (FIG. 6). Average nutrient content of the diet plans was considered to be appropriate for individuals with type-2 diabetes (Table 2).

TABLE 2

Macronutrient profile and fiber content of daily meal plans, averaged across 2 weeks.

| Score Target | Energy (kcal) | Carb. (% kcal) | Fat (% kcal) | Protein (% kcal) | Fiber (g) |
|---|---|---|---|---|---|
| 36 | 1660 | 49 | 34 | 20 | 26 |
| 45 | 1961 | 53 | 32 | 18 | 32 |
| 55 | 2401 | 55 | 30 | 18 | 38 |
| 72 | 3107 | 54 | 33 | 17 | 45 |

Diet Planning Session #2

Methods: Diet Planning Session #2 was conducted to determine the effect of adding various Rules on the nutrient profile of the planned diets. The foods database from Diet Planning Session #1 was expanded to include 1001 commonly consumed foods. Each food was assigned a Relative Food Score using Equation 16. A group of 15 individuals, composed of 4 men and 11 women, was assigned to a single Daily Score corresponding to a 2000 kilocalorie level (score=45), as shown in Table 1. The individuals were asked to plan all meals and snacks for each day of a 2 week period, using only the Relative Food Scores as the basis for diet planning. During this session, all individuals were asked to plan diets, applying Rules (blue/green, meal/snack, and fruit/vegetable; as described above) either individually, or in combination. Zero-scoring foods were always considered to be zero, regardless of the number of zero-scoring foods used during a day. Healthy eating guidelines were also provided. The resulting diet plans were summarized for their energy and nutrient content on the basis of average daily intake over the 2-week dietary planning period. Individuals were asked to rate the difficulty of implementing various rules in their diet planning.

Results: Diet plans created by participants using this scoring system were satisfactory in their energy content and macronutrient profile. Energy content of the diet plans closely reflected the target energy intake level prescribed by the assigned score of 45. Average nutrient content of the diet plans was considered to be appropriate for individuals with type-2 diabetes (Table 3). The use of no rules, or only the meal and snack score rule, was judged to be least difficult by the individuals who participated in diet planning.

TABLE 3

Macronutrient profile and fiber content of daily meal plans (Score = 45), averaged across 2 weeks.

| Rule Combination | Energy (kcal) | Carb. (% kcal) | Fat (% kcal) | Protein (% kcal) | Fiber (g) |
|---|---|---|---|---|---|
| No Rules | 1925 | 53 | 33 | 16 | 21 |
| Green/Blue Only | 1970 | 51 | 35 | 17 | 23 |
| Meal/Snack Only | 1964 | 52 | 32 | 18 | 22 |
| Fruit/Vegetable Only | 1998 | 58 | 30 | 16 | 32 |
| Green/Blue + Meal/Snack | 1994 | 51 | 34 | 18 | 24 |
| Green/Blue + Fruit/Vegetable | 2009 | 55 | 30 | 18 | 30 |
| Meal/Snack + Fruit/Vegetable | 2008 | 58 | 30 | 16 | 32 |
| All Rules | 2021 | 56 | 31 | 17 | 32 |

Diet Planning Session #3

Methods: Diet Planning Session #3 was conducted to determine whether the correlation between Daily Score and dietary energy content would be retained when only using a single Rule. The foods database from Diet Planning Session #2 was used. Each food was assigned a Relative Food Score using Equation 16. The same 15 individuals were assigned to Daily Scores corresponding to various energy levels, as shown in Table 4. The individuals were asked to plan all meals and snacks for each day of a 2 week period, using only the Relative Food Scores as the basis for diet planning. During this session only the meal/snack Rule was applied. Zero-scoring foods were always considered to be zero, regardless of the number of zero-scoring foods used during a day. Healthy eating guidelines were also provided. The resulting diet plans were summarized for their energy and nutrient content on the basis of average daily intake over the 2-week dietary planning period.

TABLE 4

Daily Scores and meal and snack scores corresponding to daily energy requirements

| Daily Energy Requirement (kcal) | Daily Score | Meal Score | Snack Score |
|---|---|---|---|
| 1600 | 35 | 10 | 5 |
| 2000 | 45 | 13 | 6 |
| 2400 | 55 | 16 | 7 |
| 3000 | 70 | 20 | 10 |

Figure 7:
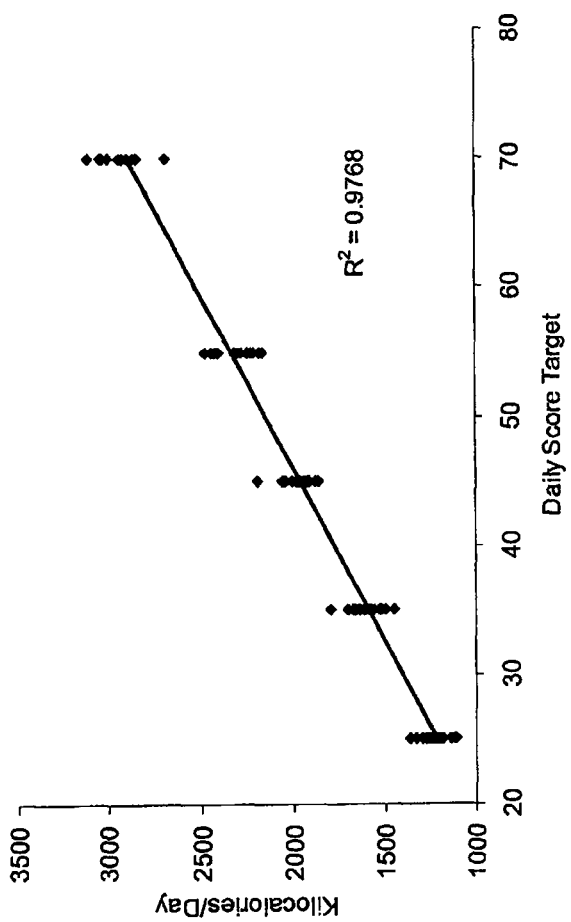
FIG. 7 shows a correlation of energy content to score target for daily meal plans, averaged across 1 week.

Results: Diet plans created using this scoring system were satisfactory in their energy content and macronutrient profile. Energy content of the diet plans closely reflected the target energy intake levels prescribed by the assigned scores (FIG. 7). Average nutrient content of the diet plans was considered to be appropriate for individuals with type-2 diabetes (Table 5).

TABLE 5

Macronutrient profile and fiber content of daily meal plans, averaged across all available weeks.

| Score Target | Energy (kcal) | Carb. (% kcal) | Fat (% kcal) | Protein (% kcal) | Fiber (g) |
|---|---|---|---|---|---|
| 25 | 1220 | 55 | 27 | 21 | 21 |
| 35 | 1594 | 53 | 31 | 18 | 21 |
| 45 | 1965 | 52 | 33 | 17 | 23 |
| 55 | 2312 | 55 | 33 | 15 | 27 |
| 70 | 2948 | 50 | 36 | 16 | 30 |

In an important aspect, the following method may be utilized for calculating scores.

If calories are <20 and total carbohydrates are <5.5, then score=0.

Otherwise, the score is calculated using one of equations 23 to 28. The $k_i$ values may range from 0 to 10 or 0 to −10, for example for fiber. The coefficient in these equations have been pre-divided by 12.15.

$$\text{Relative Score} = 0.156645669442622 * TotalFat + \quad \text{EQUATION 23}$$
$$0.00130496192617028 * Sodium +$$
$$0.03096235920085 * Sugars +$$
$$0.102463379833054 * TotalCarb -$$
$$0.181154549031557 * DietaryFiber +$$
$$0.218444033740931 * (SatFat + TFA)$$

Rounded to the nearest nonnegative integer.

(Equation for foods lacking data for TFA) EQUATION 24

$$\text{Relative Score} = 0.168120424543066 * TotalFat +$$
$$0.191832459717235 * SatFat +$$
$$0.0012871370715744 * Sodium +$$
$$0.103492811011505 * TotalCarb -$$
$$0.185204527271864 * DietaryFiber +$$
$$0.0297132567884848 * Sugars$$

Rounded to the nearest nonnegative integer.

(Equation for foods lacking data for TFA and Sugars) EQUATION 25

$$\text{Relative Score} = 0.161935991116738 * TotalFat +$$
$$0.207406290645869 * SatFat +$$
$$0.00111104498953334 * Sodium +$$
$$0.11741246378783 * TotalCarb -$$
$$0.217625438759603 * DietaryFiber$$

Rounded to the nearest nonnegative integer.

(Equation for foods lacking data for TFA and Fiber) EQUATION 26

$$\text{Relative Score} = 0.0326985155139462 * TotalFat +$$
$$0.211265063840429 * SatFat +$$
$$0.00131122105057051 * Sodium +$$
$$0.029463585398812 * TotalCarb +$$
$$0.0147759231820284 * Calories -$$
$$0.067204486301925 * Protein +$$
$$0.041943857932438 * Sugars$$

Rounded to the nearest nonnegative integer.

$$\begin{pmatrix} \text{Equation for foods lacking data for TFA,} \\ \text{Fiber and Sugars} \end{pmatrix} \quad \text{EQUATION 27}$$

$$\text{Relative Score} = 0.0448609220288849 * TotalFat +$$
$$0.239610545132076 * SatFat +$$
$$0.00102682557051393 * Sodium +$$
$$0.0583620936579316 * TotalCarb +$$
$$0.011967404042854 * Calories -$$
$$0.0522157836653316 * Protein -$$
$$0.449899235041729 * Iron‡$$

Rounded to the nearest nonnegative integer.

In Equation 27, the value for Iron represents the decimal proportion of the USDA Daily Value for Iron (e.g. the decimal proportion 0.25, as used in the above formula, would correspond to "25% DV" on a nutrition facts panel).

(Equation for foods lacking data for TFA and SatFat) EQUATION 28

$$\text{Realative Score} = 0.220546668684559 * TotalFat +$$

-continued $$0.00130891980845418 * Sodium +$$
$$0.100112811169218 * TotalCarb -$$
$$0.203608691363277 * DietaryFiber +$$
$$0.033503374531092 * Sugars +$$
$$0.000972373425585813 * Calories$$

Rounded to the nearest nonnegative integer.

| Term | Meaning | Equation where term is used | | | | | |
|---|---|---|---|---|---|---|---|
| | | Equ. 23 | Equ. 24 | Equ. 25 | Equ. 26 | Equ. 27 | Equ. 28 |
| TotalFat | Total Farry Acids (g) | X | X | X | X | X | X |
| SatFat | Saturated Fatty Acids (g) | X | X | X | X | X | |
| Sodium | Sodium, mg | X | X | X | X | X | X |
| TotalCarb | Carbohydrate (g) | X | X | X | X | X | X |
| DietaryFiber | Fiber (g) | X | X | X | | | X |
| Sugars | Sugar (g) | X | X | | X | | X |
| TFA | Trans fatty acids (g) | X | | | | | |
| Calories | Calories (kcal) | | | | X | X | X |
| Protein | Protein (g) | | | | X | X | |
| Iron | Iron, % DV expressed as a decimal proportion | | | | X | | |

In this aspect of the invention, nutrient values must correspond to the stated serving size for each food item. Missing nutrient values are not treated as zeroes in the formulas. For example, if a required nutrient value is missing, then a different formula must be used. Failing that, the relative score cannot be calculated.

In an aspect where recipe foods are used, recipe nutrient values are calculated representing the sum for all recipe ingredients. Recipe nutrient values are rescaled to correspond to the required serving size. Resulting per-serving nutrient values are entered into the appropriate formula to obtain the score.

In another aspect, equations 23-28 are not used for alcoholic beverages and the following guidelines for alcoholic beverages are followed.

The online meal planner must have the capability to track the number of servings of alcoholic beverages in the daily meal plan.

Women should limit alcohol consumption to 1 drink or less per day, and men should limit intake to 2 drinks or less per day.

One "drink" is defined as one serving size of an alcoholic beverage as indicated in the chart below. For example, one serving of beer is the equivalent of one can or bottle. Two pints of beer (16 oz each) exceeds the recommended amount and would trigger a warning.

In this aspect, if a consumer's entry exceeds the recommended intake, a pop-up warning should appear.

| Alcoholic Beverage | Serving Size | Score |
|---|---|---|
| Beer (regular) | 12 fl oz | 3 |
| Beer (light) | 12 fl oz | 2 |
| Dry Wine (red, white) | 5 fl oz | 3 |
| Distilled Spirits (vodka, rum, gin, whiskey: 80-86 proof) | 1.5 fl oz | 2 |
| Dessert Wine (sherry) | 3.5 fl oz | 4 |
| Liqueur, coffee (53 proof) | 1 fl oz | 3 |

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

As but one example in these regards, a small handheld barcode reader can be configured with an ability to submit a read barcode for a given food item to a database and to receive in turn information regarding the contents of that food item. This information can then be employed by the reader in conjunction with these teachings to calculate a corresponding relative score number for that food item. When this barcode reader comprises, for example, a cellular telephone or the like, the score number can be presented on the device's display to permit the end user to make use of that information when deciding, for example, whether to purchase this food item. By another approach, this barcode reader can have an integral label printer. In this case, a label could be printed with this score number. This label can then be attached to the food item. Such an approach would allow retail store employees to mark their food items in this way notwithstanding that the manufacturers of such items might not provide the score number.

What is claimed is:

1. A method for assisting a person to maintain a predetermined diet, the method comprising:
   determining in a processing device, a minimum and maximum relative score number effective for maintaining a predetermined diet over a period of time;
   calculating a relative score number for each of a number of possible food serving choices by fitting at least two characteristics of the possible food serving choices to a model generated by forced choice comparisons of sample food choices by a plurality of informed domain representatives;
   identifying in a computing device, food serving choices that will provide an aggregated total relative score number between the determined minimum and maximum relative score number; and
   outputting via an output device, a diet plan using the identified food serving choices to thereby assist the person to maintain the predetermined diet,
   wherein the relative score number is calculated by
   assigning a raw score comprising a fixed value when a serving portion of one of the food serving choices comprises a food or nonalcoholic beverage having 5 grams or less carbohydrates and less than 20 kilocalories;
   for a serving portion of one of the food serving choices having 3 grams of carbohydrates or more, determining protein, fiber, trans fatty acids, saturated fatty acids, total fatty acids, sodium, and vitamin values and calculating a raw score using an equation selected from the following equations:

Equation 1A defined as, $$\text{Raw Score} = k1 + k2 * \sqrt{\text{sodiummilligrams}} - k3 * \sqrt{\text{fibergrams}} -$$

$$k4*\sqrt{proteingrams}+k5*\sqrt{transfatgrams+saturatedfatgrams}+$$

$$k6*\sqrt{carbohydrategrams+proteingrams+totalfatgrams}-$$

$$k7*\sqrt{sumof\%dailyvalueforvitaminsA,C,andmineralsironandcalcium}-k8*carbohydrategrams,$$

wherein k1 is 0 to 15, k2 is 0 to 5, k3 is 0 to 15, k4 is 0 to 30, k5 is 0 to 30, k6 is 0 to 30, k7 is 0 to 10, and k8 is 0 to 10, where at least three of k1 through k8 have a value greater than 0;

Equation 1B defined as, $$\text{Raw Score}=k9+k10*\sqrt{sodiummilligrams}-k11*\sqrt{fibergrams}-$$

$$k12*\sqrt{proteingrams}+k13*\sqrt{transfatgrams+saturatedfatgrams}+$$

$$k14*\sqrt{carbohydrategrams+proteingrams+totalfatgrams}-$$

$$k15*carbohydrate\ grams,$$

wherein k9 is 0 to 20, k10 is 0 to 15, k11 is 0 to 30, k12 is 0 to 30, k13 is 0 to 30, k14 is 0 to 40, and k15 is 0 to 10, where at least three of k9 through k15 have a value greater than 0; and Equation 1C defined as, $$\text{Raw Score}=k99+k100*\sqrt{sodiummilligrams}-k101*\sqrt{fibergrams}-$$

$$k102*\sqrt{proteingrams}+k103*\sqrt{transfatgrams+saturatedfatgrams}+$$

$$k104*\sqrt{carbohydrategrams+proteingrams+totalfatgrams}-$$

$$k105*carbohydrate\ grams,$$

wherein k99 is 0 to 45, k100 is 0 to 5, k101 is 0 to 30, k102 is 0 to 20, k103 is 0 to 30, k104 is 0 to 40, and k105 is 0 to 10, where at least three of k99 through k105 have a value greater than 0;

for a serving portion of one of the food serving choices having less than 3 grams of carbohydrates, determining protein, saturated fatty acids, total fatty acids, calcium and sodium values and calculating a raw score using Equation 2 defined as, $$\text{Raw Score}=k16+k17*\sqrt{totalfatgrams}+$$

$$k18*\sqrt{transfatgrams+saturatedfatgrams}+$$

$$k19*\sqrt{sodiummilligrams}-k20*\sqrt{proteingrams}-$$

$$k21*calcium\ milligrams,$$

wherein k16 is 0 to 45, k17 is 0 to 20, k18 is 0 to 20, k19 is 0 to 5, k20 is 0 to 20, and k21 is 0 to 10, where at least three of k16 through k21 have a value greater than 0;

when a serving portion of one of the food serving choices comprises a nonalcoholic beverage having 20 kilocalories or more, determining sugar, total fatty acids, calcium, and vitamin values and calculating a raw score using Equation 3 defined as, $$\text{Raw Score}=k22+k23*\sqrt{totalfatgrams}-$$

$$k24*\sqrt{calciummilligrams}+k25*\sqrt{sugargrams}-$$

$$k26*\sqrt{sumof\%dailyvalueforvitaminsA,C,andmineralsironandcalcium},$$

wherein k22 is 0 to 90, k23 is 0 to 30, k24 is 0 to 20, k25 is 0 to 20, and k26 is 0 to 20, where at least three of k22 through k26 have a value greater than 0; and when a serving portion of one of the food serving choices comprises an alcoholic beverage, determining a raw score using Equation 4 defined as, $$\text{Raw Score}=k27*\sqrt{numberofservingofalcoholicbeverage},$$

wherein k27 is 0 to 100.

2. The method of claim 1 wherein the informed domain representatives are dietary experts.

3. The method of claim 1 wherein the predetermined diet is selected from the group consisting of diets for diabetes, heart disease, blood pressure management, metabolic syndromes, weight management, healthy aging, cognition and cancer prevention.

4. The method of claim 1 further comprising the step of labeling at least one of the food serving choices with the relative score number for the respective food serving choice.

* * * * *